United States Patent
Felton et al.

(10) Patent No.: US 11,923,876 B2
(45) Date of Patent: Mar. 5, 2024

(54) SYSTEMS, METHODS, AND MEDIA FOR LOW-POWER ENCODING OF CONTINUOUS PHYSIOLOGICAL SIGNALS IN A REMOTE PHYSIOLOGICAL MONITOR

(71) Applicant: Mayo Foundation for Medical Education and Research, Rochester, MN (US)

(72) Inventors: Christopher L. Felton, Rochester, MN (US); Barry K. Gilbert, Rochester, MN (US); Clifton R. Haider, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 570 days.

(21) Appl. No.: 17/260,396

(22) PCT Filed: Jul. 15, 2019

(86) PCT No.: PCT/US2019/041817
§ 371 (c)(1),
(2) Date: Jan. 14, 2021

(87) PCT Pub. No.: WO2020/018428
PCT Pub. Date: Jan. 23, 2020

(65) Prior Publication Data
US 2021/0306000 A1 Sep. 30, 2021

Related U.S. Application Data

(60) Provisional application No. 62/698,784, filed on Jul. 16, 2018.

(51) Int. Cl.
*H03M 7/00* (2006.01)
*A61B 5/00* (2006.01)
(Continued)

(52) U.S. Cl.
CPC ......... *H03M 7/6047* (2013.01); *A61B 5/0205* (2013.01); *A61B 5/318* (2021.01);
(Continued)

(58) Field of Classification Search
CPC .... H03M 7/6047; H03M 7/3079; H03M 7/70; A61B 5/318; A61B 5/0205; A61B 5/7232
(Continued)

(56) References Cited

U.S. PATENT DOCUMENTS

2008/0051839 A1* 2/2008 Libbus ............... A61B 5/02028
607/2
2012/0133532 A1 5/2012 Hunt
(Continued)

FOREIGN PATENT DOCUMENTS

WO 2011131248 A1 10/2011
WO 2017146886 A1 8/2017

OTHER PUBLICATIONS

Akimura, D. et al, "Compressed sensing method for human activity sensing using mobile phone accelerometers," in 2012 Ninth International Conference on Networked Sensing (INSS), Jun. 2012, pp. 1-4.
(Continued)

*Primary Examiner* — Peguy Jean Pierre
(74) *Attorney, Agent, or Firm* — Quarles & Brady LLP

(57) ABSTRACT

In accordance with some embodiments of the disclosed subject matter, mechanisms (which can, for example, include systems, methods, and media) for low-power encoding of continuous physiological signals are provided. In some embodiments, a system comprises: a physiological sensor; and a remote monitor comprising: a battery; memory storing a k-ary tree including a root with k branches corresponding to k delta values, k nodes at a first depth below the Leads root node each having k branches corresponding to
(Continued)

the k delta values the nodes indexed to indicate the lateral position of the node within the depth; a processor programmed to: receive a first sample value from the sensor; receive a second sample value; calculate a difference between the second first sample values; determine that the delta corresponds to a first delta of the k delta values; encode a sequence of deltas based on a depth and node index.

20 Claims, 19 Drawing Sheets

(51) Int. Cl.
    *A61B 5/0205*     (2006.01)
    *A61B 5/318*     (2021.01)
    *H03M 7/30*     (2006.01)

(52) U.S. Cl.
    CPC .......... *A61B 5/7232* (2013.01); *H03M 7/3079* (2013.01); *H03M 7/70* (2013.01); *A61B 2560/0214* (2013.01); *A61B 2562/0219* (2013.01)

(58) Field of Classification Search
    USPC ........................................ 341/50, 51, 106, 60
    See application file for complete search history.

(56) References Cited

U.S. PATENT DOCUMENTS

2018/0220997 A1    8/2018  Song
2020/0138291 A1*  5/2020  Bardy .................... A61B 5/259

OTHER PUBLICATIONS

Anonymous. Mayo clinic studies climbers on everest to help heart patients at home. Published Mar. 22, 2012. [Online]. Available: https://web.archive.org/web/20121023112455/http://press.nationalgeographic.com/2012/05/26/natgeo-and-the-north-face-expedition-reaches-everest-summit/.

Anonymous. National geographic and the north face expedition to mount everest reaches summit. May 26, 2012. [Online]. Available: http://press.nationalgeographic.com/2012/05/26/natgeo-and-the-north-face-expedition-reaches-everest-summit/.

Burguera A. et al, "Fast qrs detection and ecg compression based on signal structural analysis," IEEE Journal of Biomedical and Health Informatics, vol. PP, No. 99, pp. 1-1, 2018.

Chua, E. et al, "Vlsi implementation of a mixed bio-signal lossless data compressor for portable brain-heart monitoring systems," in 2011 IEEE International Conference on Consumer Electronics (ICCE), Jan. 2011, pp. 557-558.

Dai C. et al, "A lossless data reduction technique for wireless eeg recorders and its use in selective data filtering for seizure monitoring," in 2015 37th Annual International Conference of the IEEE Engineering in Medicine and Biology Society (EMBC), Aug. 2015, pp. 6186-6189.

Deepu, C.J. et al, "A 3-lead ecg-onchip with qrs detection and lossless compression for wireless sensors," IEEE Transactions on Circuits and Systems II: Express Briefs, vol. 63, No. 12, pp. 1151-1155, Dec. 2016.

Dixon, A.M.R et al, "Compressed sensing system considerations for ecg and emg wireless biosensors," IEEE Transactions on Biomedical Circuits and Systems, vol. 6, No. 2, pp. 156-166, Apr. 2012.

Felton, C.L. et al, "A comparison of efficient first stage decimation filters for delta sigma modulators," 2017 51st Asilomar Conference on Signals, Systems, and Computers. IEEE, 2017.

Gilbert, B.K. et al, "A Measurement-Quality Body-Worn Sensor-Agnostic Physiological Monitor for Biomedical Applications," American Journal of Biomedical Engineering, vol. 5, No. 2, pp. 34-66, 2015.

Hamilton et al. "Compression of the ambulatory ecg by average beat subtraction and residual differencing," IEEE Transactions on Biomedical Engineering, vol. 38, No. 3, pp. 253-259, Mar. 1991.

Holmes III, D. et al, "Efficient Implementation of Stockwell Transform for Real-Time Embedded Processing of Physiological Signals," in Engineering in Medicine and Biology Society (EMBC), 2017 IEEE 39th Annual International Conference of the, 2017.

Hunter J.D., "Matplotlib: A 2d graphics environment," Computing In Science & Engineering, vol. 9, No. 3, pp. 90-95, 2007.

International Searching Authority. International Search Report and Written Opinion for application PCT/US2019/041817, dated Jan. 16, 2020. 18 pages.

Kim, H. et al, "A low energy bio sensor node processor for continuous healthcare monitoring system," in 2008 IEEE Asian Solid-State Circuits Conference, Nov. 2008, pp. 317-320.

Leon-Salas, W.D. "Low-complexity compression for sensory systems," IEEE Transactions on Circuits and Systems II: Express Briefs, vol. 62, No. 4, pp. 322-326, Apr. 2015.

Luharuka, R. et al. "Design and realization of a portable data logger for physiological sensing [gsr]," IEEE Transactions on Instrumentation and Measurement, vol. 52, No. 4, pp. 1289-1295, Aug. 2003.

Moody G.B. et al, "The Impact of the MIT-BIH Arrhythmia Database," IEEE Engineering in Medicine and Biology Magazine, vol. 20, No. 3, pp. 45-50, 2001.

Pinto, S. et al, "Clinical accuracy qrs detector with automatic parameter adjustment in an autonomous," Nov. 2017.

Smith, S.W. Delta Encoding section of Chapter 27: Data Compression in The Scientist and Engineer's Guide to Digital Signal Processing. Available online at https://www.dspguide.com/ch27/4.htm. Accessed on Jan. 30, 2018.

Song, P. et al. "Ultrasound Small Vessel Imaging with Block-Wise Adaptive Local Clutter Filtering," IEEE Transactions on Medical Imaging, vol. 36, pp. 251-262, 2017.

Tseng, C.K. et al, "A takagi-sugeno fuzzy neural network-based predictive coding scheme for lossless compression of ecg signals," in TENCON 2017—2017 IEEE Region 10 Conference, Nov. 2017, pp. 1646-1660.

Vale, L. et al, "Lifestream: Real-time bio-signal remote monitoring system," in 2010 4th International Conference on Bioinformatics and Biomedical Engineering, Jun. 2010, pp. 1-4.

Wikipedia. Run Length Encoding. Accessed on Jan. 30, 2018 at https://en.wikipedia.org/wiki/Run-length_encoding. 3 pages.

Wikipedia, Huffman coding. Accessed on Oct. 2, 2023 at https://en.wikipedia.org/w/index.php? title=Huffman_coding&oldid=849967936, 6 pages.

Hessar, F et al., "Mininum energy source coding for asymmetric modulation with application to RFID", 2013 IEEE International Conference on RFID, IEEE, Apr. 30, 2013, pp. 207-214.

* cited by examiner

TABLE I
ENCODING RESULTS ON EVEREST RECORDED DATA

| Device | ECG CR | ECG Reduction | Motion CR | Motion Reduction |
|---|---|---|---|---|
| 1112_0012 | 1.38 | 27.5% | 2.24 | 55.4% |
| 1212_0024 | 1.52 | 34.2% | 1.96 | 49.0% |
| 1212_0026 | 1.30 | 23.1% | 1.98 | 49.5% |
| 1212_0027 | 1.43 | 30.1% | 1.90 | 47.4% |
| 1312_0029 | 1.31 | 23.7% | 1.84 | 45.7% |
| 1312_0031 | 1.45 | 31.0% | 1.81 | 44.8% |
| 1312_0038 | 1.37 | 27.0% | 2.01 | 50.2% |
| 1312_0041 | 1.35 | 25.9% | 1.92 | 47.9% |
| 1312_0043 | 1.52 | 34.2% | 2.24 | 55.4% |

TABLE II
ENCODING RESULTS ON MIT-BIH ECG DATABASE

| Record | CR | Reduction |
|---|---|---|
| 100 | 1.83 | 45.5% |
| 102 | 1.82 | 45.1% |
| 107 | 1.61 | 33.3% |
| 118 | 1.50 | 37.8% |
| 205 | 1.91 | 47.7% |
| 213 | 1.49 | 32.9% |
| 231 | 1.84 | 45.5% |

TABLE III
LOSSLESS ENCODING METHOD COMPARISONS

| Method | Signals | CR min | CR max |
|---|---|---|---|
| First difference (delta) [19] | GSR | 3.9 | 3.9 |
| Huffman linear predict [20] | Bio-signals | 2.0 | 2.0 |
| DPCM predictor [14] | EEG, ECG | 1.7 | 2.5 |
| Log2-subband [15] | EEG | 1.7 | 2.8 |
| Adaptive linear predictor [16] | ECG | 2.2 | 2.2 |
| Proposed | ECG, Motion | 1.3 | 2.2 |

FIG. 15

SYSTEMS, METHODS, AND MEDIA FOR LOW-POWER ENCODING OF CONTINUOUS PHYSIOLOGICAL SIGNALS IN A REMOTE PHYSIOLOGICAL MONITOR

CROSS-REFERENCE TO RELATED APPLICATIONS

This application is a 371 U.S. National Phase Entry of International Application No. PCT/US2019/041817, filed Jul. 15, 2019, which claims the benefit of U.S. Provisional Patent Application No. 62/698,784, filed Jul. 16, 2018, which is hereby incorporated herein by reference in its entirety for all purposes.

STATEMENT REGARDING FEDERALLY SPONSORED RESEARCH

N/A

BACKGROUND

In general, while advances in computing power and storage can allow remote physiological monitors to collect vast amounts of data, these devices generally have small form factors and correspondingly small batteries. This can lead to battery life on the order of hours to days, which may be shorter than the desired battery life for many applications. This relatively short battery life may require a user to remove the device to change or recharge the battery often, causing inconvenience and potentially leading to the user abandoning use of the remote physiological monitor.

Additionally, even if storage is relatively inexpensive in dollar and space terms, if the physiological monitor captures data from many different sensors that are sampled several times per second this can generate relatively large amounts of data when compared to the capacity of a relatively low-power and small form factor storage device. This may limit the ability to feasible store all desired data using local (e.g., built-in) storage without compression. While lossless compression can reduce the amount of local storage required to store a given amount of data, many lossless compression techniques are computationally intensive, causing an increased drain on the battery.

Accordingly, new systems, methods, and media for low-power encoding of continuous physiological signals in a remote physiological monitor are desirable.

SUMMARY

In accordance with some embodiments of the disclosed subject matter, systems, methods, and media for low-power encoding of continuous physiological signals in a remote physiological monitor are provided.

In accordance with some embodiments of the disclosed subject matter, a system for low-power encoding of continuous physiological signals is provided, the system comprising: a sensor; and a remote physiological monitor comprising: a battery; memory storing a k-ary tree, the k-ary tree including a root node with k branches corresponding to k delta values, k nodes at a first depth below the root node each having k branches corresponding to the k delta values, and $k^2$ nodes at a second depth below the root node each having k branches corresponding to the k delta values, wherein the nodes at each depth are indexed such that each node is associated with an index number indicating that node's lateral position within that depth of the k-ary tree; a processor coupled to the sensor, the processor programmed to: receive a first signal from the sensor at a first time, the first signal corresponding to a first sample value; receive a second signal from the sensor at a second time, the second signal corresponding to a second sample value; calculate a difference between the second sample value and the first sample value, the difference corresponding to a first delta value; determine that the first delta value corresponds to a first particular delta value of the k delta values; in response to determining that the first delta value corresponds to the first particular delta value, store a first depth and a first node index of a child node at the end of the branch corresponding to the first particular delta value; receive a third signal from the sensor at a third time, the third signal corresponding to a third sample value; calculate a difference between the third sample value and the second sample value, the difference corresponding to a second delta value; determine that the second delta value corresponds to a second particular delta value of the k delta values; in response to determining that the second delta value corresponds to the second particular delta value, store a second depth and a second node index of a child node at the end of the branch corresponding to the second particular delta value; and encode the sequence of the first delta value and the second delta value based on the second depth and the second node index.

In some embodiments, the sensor comprises an electrocardiogram lead, and the first signal is an analog signal.

In some embodiments, the sensor comprises an accelerometer, and the first signal is a digital signal.

In some embodiments, the processor is further programmed to: receive a fourth signal from the sensor at a fourth time, the fourth signal corresponding to a fourth sample value; calculate a difference between the fourth sample value and the third sample value, the difference corresponding to a third delta value; and determine that the third delta value does not correspond to any of the k delta values.

In some embodiments, the processor is further programmed to: encode the sequence of the first delta value and the second delta value in response to the determination that the third delta value does not correspond any of the k delta values.

In some embodiments, the processor is further programmed to: determine that the node at the second depth and the second node index does not have any branches; and in response to determining that the node at the second depth and the second node index does not have any branches, encode the sequence of the first delta value and the second delta value.

In some embodiments, the processor is further programmed to: in response to determining that the third delta value does not correspond any of the k delta values, compare the minimum number of bits required to represent the third delta value to a first number of bits of a first fixed bit length token $\delta_B$ to determine whether the minimum number of bits is greater than the first number of bits.

In some embodiments, the processor is further programmed to: in response to determining that the minimum number of bits is less than or equal to the first number of bits, encode the third delta value as a $\delta_B$ token.

In some embodiments, the processor is further programmed to: in response to determining that the minimum number of bits is greater than the first number of bits, compare the minimum number of bits required to represent the third delta value to a second number of bits of a second fixed bit length token $\delta_C$ to determine whether the minimum number of bits is greater than the second number of bits.

In some embodiments, the processor is further programmed to: in response to determining that the minimum number of bits is less than or equal to the second number of bits, encode the third delta value as a $\delta_C$ token.

In some embodiments, the processor is further programmed to: in response to determining that the minimum number of bits is greater than the second number of bits, encode the fourth sample value as a sample token.

In some embodiments, the processor comprises an application-specific integrated circuit.

In accordance with some embodiments of the disclosed subject matter, a method for choosing the branch values for a k-ary tree is provided, the method comprising: obtaining a statistically significant sample of an input stream to be encoded; encoding the input stream using a first set of k-ary branch values; encoding the input stream using a second set of k-ary branch values; determining that an amount of energy used to encode the input stream using the first set of k-ary values is lower than an amount of energy used to encode the input stream using the second set of k-ary values; selecting the first set of k-ary branch values based at least in part on the determination that the amount of energy used to encode the input stream using the first set of k-ary values is lower than the amount of energy used to encode the input stream using the second set of k-ary values; and constructing a k-ary tree based on the first set of k-ary branch values for use in an encoder of a physiological monitoring system.

In accordance with some embodiments of the disclosed subject matter, a method for low-power encoding of continuous physiological signals is provided, the method comprising: receiving a first signal from a sensor at a first time, the first signal corresponding to a first sample value; receiving a second signal from the sensor at a second time, the second signal corresponding to a second sample value; calculating a difference between the second sample value and the first sample value, the difference corresponding to a first delta value; determining that the first delta value corresponds to a first particular delta value of k delta values of a k-ary tree, the k-ary tree including a root node with k branches corresponding to k delta values, k nodes at a first depth below the root node each having k branches corresponding to the k delta values, and $k^2$ nodes at a second depth below the root node each having k branches corresponding to the k delta values, wherein the nodes at each depth are indexed such that each node is associated with an index number indicating that node's lateral position within that depth of the k-ary tree; in response to determining that the first delta value corresponds to the first particular delta value, storing a first depth and a first node index of a child node at the end of the branch corresponding to the first particular delta value; receiving a third signal from the sensor at a third time, the third signal corresponding to a third sample value; calculating a difference between the third sample value and the second sample value, the difference corresponding to a second delta value; determining that the second delta value corresponds to a second particular delta value of the k delta values; in response to determining that the second delta value corresponds to the second particular delta value, storing a second depth and a second node index of a child node at the end of the branch corresponding to the second particular delta value; and encoding the sequence of the first delta value and the second delta value based on the second depth and the second node index.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 15 shows a first table of compression ratios and data reductions realized by applying techniques described herein to encode data collected by various remote physiological monitors while subjects attempted to climb Mount Everest; a second table of compression ratios and data reductions realized by applying techniques described herein to encode ECG data collected from various subjects; and a third table comparing compression ratios of various conventional encoding schemes, and the techniques described herein for low-power encoding of continuous physiological signals in a remote physiological monitor.

DETAILED DESCRIPTION

Figure 1:
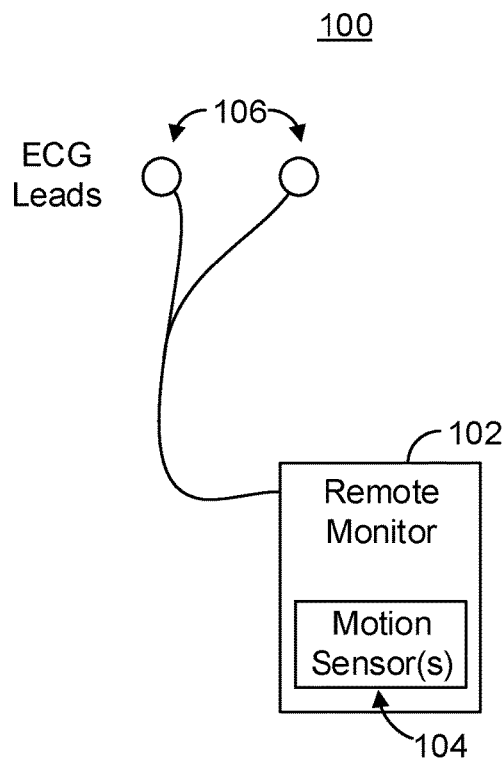
FIG. 1 shows an example of a system for low-power encoding of continuous physiological signals in a remote physiological monitor in accordance with some embodiments of the disclosed subject matter.

In accordance with various embodiments, mechanisms (which can, for example, include systems, methods, and media) for low-power encoding of continuous physiological signals in a remote physiological monitor are provided.

In recent years, continuous remote physiologic and environmental monitoring through the use of an increasing array of sensors has become more common. Given the amount of data being digitized, processes that scale with the amount of data being collected, and that consume relatively large amounts of energy, such as data storage processes and data transmission processes, can be targeted as areas where reductions in energy can lead to improved device runtimes. For example, using inline low energy data compression techniques can increase device runtime without otherwise affecting the form factor of the remote monitor.

In many applications, the ability of remote monitors to capture physiological and/or environmental data over extended periods of time can be important for understanding underlying medical or stress-related conditions. Accordingly, for remote monitors to be effective it is typically preferable that they be unobtrusive (i.e., small in size), and have long run-times (i.e., long battery-life). These features can facilitate high deployment usability, and the ability to record weeks to months of raw physiological and/or environmental signals. Further, because acquired signals are often used for post-hoc analysis, such remote monitors are often require to continuously record samples from the sensors, rather than selectively sampling signals (e.g., recording only when there is minimal motion, or recording using an arbitrary fractional duty cycle), as a rare event or correlation between conditions may fail to be recorded. Additionally, low complexity embedded data compression techniques can significantly add to the usefulness and flexibility of such systems by reducing the impact of increasing data storage and transmission on device runtime.

In one particular application, low complexity and low power embedded data compression techniques can extend the runtime of autonomous physiologic monitors. For example, during a 2012 Mount Everest expedition, physiologic data was collected under Human Subject Internal Review Board approval from a group of novice and professional climbers using a low-power remote monitor. The device included an 8 g tri-axial accelerometer that generated ten samples per second per axis to track motion, and a custom low power single-lead pair ECG circuit that generated about 400 samples per second. Each enrolled individual wore two wet ECG electrodes positioned to capture ECG signals without affecting human performance, with the device secured in a purpose-specific pocket of a tight-fitting base-layer garment. These monitoring devices (sometimes referred to herein as Everest devices) were configured to collect all signals continuously without intervention by the user for at least two weeks. The expert climbers summited Everest, while the novice climbers only reached Everest Base Camp. It was apparent during the expedition that the most obvious limitation of the device was its constrained runtime, attributed to the desired continuous data acquisition, small battery capacity, and lack of data compression.

Capturing and recording physiological data would benefit from more effective embedded storage. For example, a low overhead compression encoding scheme can enable longer run-times for remote sensing by decreasing the amount of data that has to be stored, and thereby reducing the amount of power consumed when writing the data to non-volatile storage. In such an example, characteristics that increase the usefulness of a reference remote physiologic or environmental monitor can include: use of lossless compression; reduced encoding complexity; a reduction in the data rate being stored; and limited a priori knowledge of the data being encoded (e.g., unlike what is required for some techniques, such as Huffman coding, which relies on knowing the precise frequencies at which various values appear in the data to be compressed).

In accordance with some embodiments of the disclosed subject matter, the mechanisms described herein can be used to implement a remote physiological monitor with extended run time through use of low complexity designate delta transition (DDT) encoding techniques that achieve nearly two-fold data compression rates (compared to uncompressed storage) with a minimal energy consumption penalty. The mechanisms described herein can be used to increase run time for various embedded applications.

To extend battery life of a remote monitor, the benefits to the remote monitor generated by data compression due to lower energy costs to store data must outweigh the cost of the encoding process itself. Accordingly, as the energy required to execute an encoding technique decreases and/or as the rate of compression increases, the effect on battery life generally improves, and thus offers benefits for remote monitoring applications.

In accordance with some embodiments, the mechanisms described herein can encode a signal by: computing the change between the most recent sample and the previous sample (sometimes referred to herein, and elsewhere, as the delta, or δ, between the two values); determining which of four token types (described in more detail below) to use to encode the delta if the determined token type is encoded based on a sequence of deltas (e.g., using a k-nary as described below in connection with FIGS. 6A and 6B), the mechanisms can map the delta to a set of unsigned values representing both positive and negative deltas (e.g., as described below in connection with 712 of FIG. 7); the mechanisms can then determine which node to move to in the k-nary tree based on which branch from a current node corresponds to the unsigned value representing the delta; if there is a corresponding branch, the mechanisms can update a current value of the cursor (i.e., the current node location, e.g., as a height and index as described below in connection with FIG. 6B) being used to encode a sequence of deltas (e.g., to reflect the level and index of the new node, as described below in connection with FIG. 6B); otherwise, if there is not a next branch, saving the current value of the token; and recording a new sample and returning to calculate a new delta.

In general, delta encoding-based compression can be based on encoding the deltas between samples, instead of the absolute values of the samples. For example, as described below in connection with FIG. 11, a large proportion of the data from a physiological and/or environmental monitor may be included in a relatively narrow delta range when referenced to the previous sample. However, delta encoding by itself is insufficient, as can be appreciated based on the ECG delta distribution shown in FIG. 11: This data would not compress significantly once the overhead of the exceptions (i.e., changes outside the maximum delta change) are accounted for, or by simply compressing with a differential pulse-code modulation (DPCM) encoding.

In some embodiments, the mechanisms described herein can encode deltas using a variety of different tokens, which can include a sample token and various different delta tokens. In some embodiments, a binary two-bit delimiter can be used to identify which token is being used (e.g., "00" can correspond to a first token, "01" to a second token, etc.). Note that a token representing a sequence of deltas (e.g., by referencing the height and index of a node in a k-ary tree, as described below in connection with FIG. 6B), the number of bits in the token can be determined based on the height, as each height has a particular number of index values (corresponding to a fixed number of bits). For example, the height can be represented using a fixed number of bits based on the height of the k-ary tree (e.g., if the tree has five levels, 3 bits can be used to represent the height), and each height can be associated with a number of bits used to represent the index at that height (e.g., the index for the second level can be 2 bits, and the index for the third level can be 4 bits, such that index 1 is represented as "0001," index 5 is represented as "0101," etc.). A sample token can be a binary encoding of the sample with the delimiter (e.g., a 16 bit encoding representing the measured value, not the delta from a previous value). The sample token can have an inflation of $$1 - \frac{b_S + 2}{b_S}$$

where $b_S$ is the number of bits in a sample. Because the sample token represents an increase in data to be stored when paired with the delimiter (i.e., a compression ratio of less than one), the encoding is more efficient the less often the sample token appears. Two fixed length tokens, $\delta_A$ and $\delta_B$, can be used to represent deltas that can be represented by less than a particular number of bits. For example, the $\delta_A$ token can be about 75% of the $b_S$ size (e.g. 12 bits for the delta if the sample size is 16 bits), and the $\delta_A$ token can be about one third of the size of $b_S$ (e.g., 6 for the delta if the sample size is 16 bits, or 37.5%). A variable length token, $\delta_C$, can be used to represent a sequence of deltas that can be encoded based on a k-ary delta tree. For example, the SC token and be a variable-length token that encodes a sequence of delta transitions through a k-ary tree (e.g., as described below in connection with FIGS. 6A and 6B). Although specific examples of lengths are described herein, these are merely examples, and the parameters for the delta tokens can be adjusted based on the general statistics of the data expected to be in the data set.

Note that although the samples, changes between samples, and tokens used for encoding are described herein as samples, deltas, and $\delta_A$, $\delta_B$, $\delta_C$, and sample tokens, respectively, this is merely one example of a semantic description of these various data, and these data can be described using other language. For example, data values can be represented using the symbol V. As another example, the difference between successive data values can be represented using the symbol $\delta$. As yet another example, a mapped representation of a $\delta$ value can be represented by the symbol $\delta^M$. As still another example, data elements can be designated as tokens that can be differentiated by a subscript. In a more particular example, a $Tok_K$ token can represent a sequence of changes in sample values (i.e., a sequence of (values) indicating that the token represents a position within a k-ary tree. As another more particular example, $Tok_V$ can represent a full-width Sample Value (V). As yet another more particular example, $Tok_n$, (n=0, 1, 2, . . . ) can represent a fixed length token representing a $\delta$ that can be represented using no more than a particular number of bits (e.g., as described below in connection with FIG. 5C). Note also that subscripts can be used to denote a sequence or ordering of values or tokens. For example, a value, a precursor value, and a successor value can be represented as $\{V_N, V_{N-1}, V_{N+1}\}$. These forms of representing the underlying data are used for convenience and other notations can be used to represent the underlying data elements.

FIG. 1 shows an example 100 of a system for low-power encoding of continuous physiological signals in a remote physiological monitor in accordance with some embodiments of the disclosed subject matter. As shown in FIG. 1, system 100 can include a remote physiological monitor 102 configured to sense and record signals from one or more motions sensors 104, and one or more electrocardiogram (ECG) leads 106, for detecting motion along (e.g., along each of an X, Y, and Z axis) and electrical activity associated with a subject's heart, respectively. In some embodiments, one or more sensors (e.g., ECG lead 106) can be exterior to remote monitor 102, and one or more other sensors (e.g., motion sensor 104) can be integrated into remote monitor 102. In some embodiments, remote monitor 102 can be configured to be worn by a subject to be monitored (e.g., within a pocket of a tight fitting garment) such that information about the subject can be continuously collected.

Figure 2:
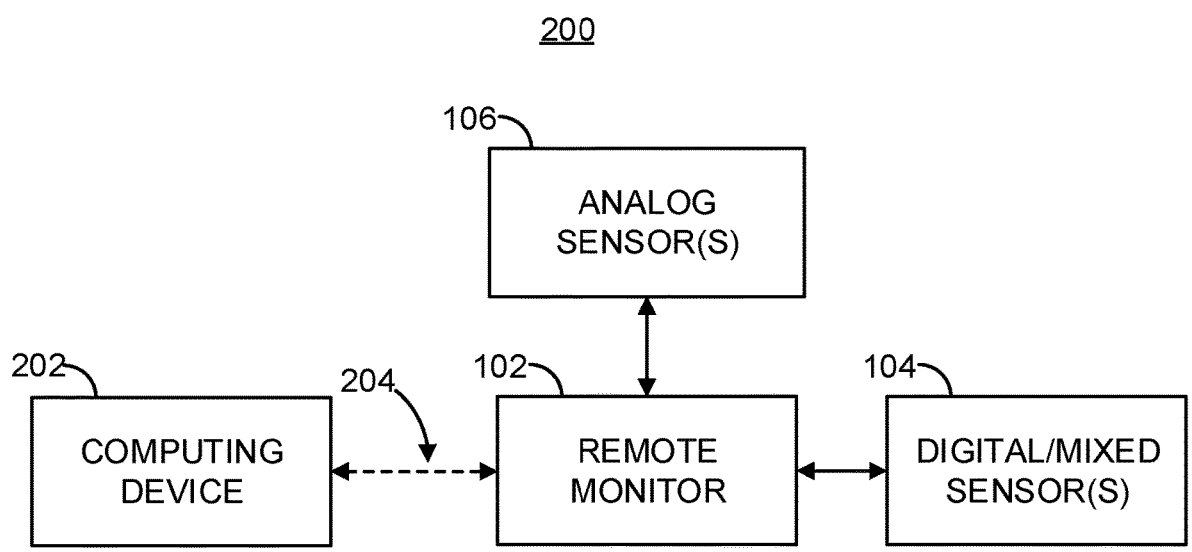
FIG. 2 shows an example of a block diagram of a system for low-power encoding of continuous physiological signals in a remote physiological monitor in accordance with some embodiments of the disclosed subject matter.

FIG. 2 shows an example 200 of a block diagram of a system for low-power encoding of continuous physiological signals in a remote physiological monitor in accordance with some embodiments of the disclosed subject matter. As shown in FIG. 2, in some embodiments, remote monitor 102 can be coupled to any suitable number of digital and/or mixed sensors (e.g., sensors that provide a digital signal indicative of an output, but which may internally produce analog signals, such as motion sensor(s) 104), and/or any suitable number of analog sensors (e.g., sensors that provide an analog signal, such as ECG leads 106). Additionally, in some embodiments, remote monitor 102 can communicate with a computing device 202 via a communication link 204 using any suitable technique or combination of techniques. For example, communication link 204 can be a wired or wireless link through which remote monitor 102 can provide recorded data (e.g., encoded using the mechanisms described herein).

Figure 3:
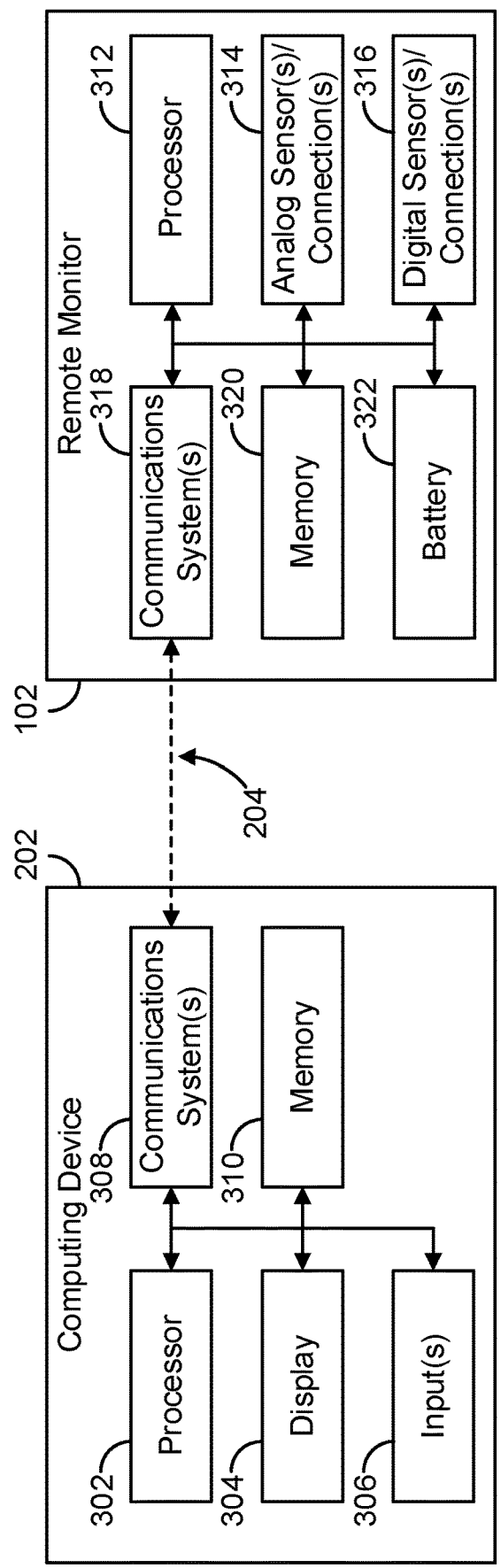
FIG. 3 shows an example of hardware that can be used to implement a remote monitor and a computing device of FIG. 2 in accordance with some embodiments of the disclosed subject matter.

FIG. 3 shows an example 300 of hardware that can be used to implement remote monitor 102 and computing device 202 of FIG. 2 in accordance with some embodiments of the disclosed subject matter. As shown in FIG. 3, in some embodiments, remote monitor 102 can include a processor 312, one or more analog sensors 314 (and/or hardware configured to receive signals from one or more analog sensors), one or more digital sensors and/or mixed sensors 316 (and/or hardware configured to receive signals from one or more digital or mixed sensors), one or more communication systems 318, memory 320, and/or a battery (and/or other power source) 322.

In some embodiments, processor 312 can be any suitable hardware processor or combination of processors, such as a central processing unit (CPU), a graphics processing unit (GPU), a microcontroller (MCU), a field programmable gate array (FPGA), an application-specific integrated circuit (ASIC), etc. In some embodiments, communications system(s) 318 can include any suitable hardware, firmware, and/or software for communicating information to computing device 202, over communication link 204, over any other suitable communication link or combination of communication links, and/or over any suitable communication network or combination of networks. For example, communications system(s) 318 can include one or more transceivers, one or more communication chips and/or chip sets, etc. In a more particular example, communications system(s) 318 can include hardware, firmware and/or software that can be used to communicate data over a coaxial cable, a fiber optic cable, an Ethernet connection, a USB connection, to establish a Wi-Fi connection, a Bluetooth connection, a cellular connection, etc.

In some embodiments, memory 320 can include any suitable storage device or devices that can be used to store instructions, values, etc., that can be used, for example, by processor 312 to receive signals via analog sensors 314 and/or digital sensors 316, to encode signals received via analog sensors 314 and/or digital sensors 316, to store the encoded signals in memory 320, and/or transmit the encoded signals to computing device 202 via communications system(s) 318, etc. Memory 312 can include any suitable volatile memory, non-volatile memory, storage, or any suitable combination thereof. For example, memory 310 can include RAM, ROM, EEPROM, one or more flash drives, one or more hard disks, one or more solid state drives, one or more optical drives, etc. In some embodiments, memory 320 can have encoded thereon a program for controlling operation of processor 312 to record encoded physiological and/or environmental signals. In some such embodiments, processor 312 can execute at least a portion of the program to execute at least a portion of process 700 as described below in connection with FIG. 7.

In some embodiments, computing device 202 can include a processor 302, a display 304, one or more inputs 306, one or more communication system(s) 308, and/or memory 310. In some embodiments, processor 302 can be any suitable hardware processor or combination of processors, such as a CPU, a GPU, MCU, FPGA, ASIC, etc. In some embodiments, display 304 can include any suitable display devices, such as a computer monitor, a touchscreen, a television, etc. In some embodiments, inputs 306 can include any suitable input devices and/or sensors that can be used to receive user input, such as a keyboard, a mouse, a touchscreen, a microphone, etc.

In some embodiments, communications system(s) 308 can include any suitable hardware, firmware, and/or software for communicating with remote monitor 102, for communicating information over communication link 204, and/or for communicating over any other suitable communication links and/or communication networks. For example, communications system(s) 308 can include one or more transceivers, one or more communication chips and/or chip sets, etc. In a more particular example, communications systems 308 can include hardware, firmware and/or software that can be used to establish a coaxial connection, a fiber optic connection, an Ethernet connection, a USB connection, a Wi-Fi connection, a Bluetooth connection, a cellular connection, etc.

In some embodiments, memory 310 can include any suitable storage device or devices that can be used to store instructions, values, etc., that can be used, for example, by processor 302 to present content using display 304, to communicate with one or remote monitors (e.g., remote monitor 102). Memory 310 can include any suitable volatile memory, non-volatile memory, storage, or any suitable combination thereof. For example, memory 310 can include RAM, ROM, EEPROM, one or more flash drives, one or more hard disks, one or more solid state drives, one or more optical drives, etc. In some embodiments, memory 310 can have encoded thereon a computer program for controlling operation of processor 302. In some such embodiments, processor 302 can execute at least a portion of the computer program to receive encoded signals from remote monitor 102, to decode the encoded data, etc. In some embodiments, processor 302 can execute one or more portions of process 700 described below in connection with FIG. 7. In some embodiments, computing device 202 can be any suitable computing device or combination of computing devices, such as a personal computer, a laptop computer, a tablet computer, a smartphone, a wearable computer, a server, etc.

Although not shown, in some embodiments, communication link 204 can include multiple communication links that form a portion of any suitable communication network or combination of communication networks. For example, communication link 204 can be a combination of one or more links in a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc.

Figure 4:
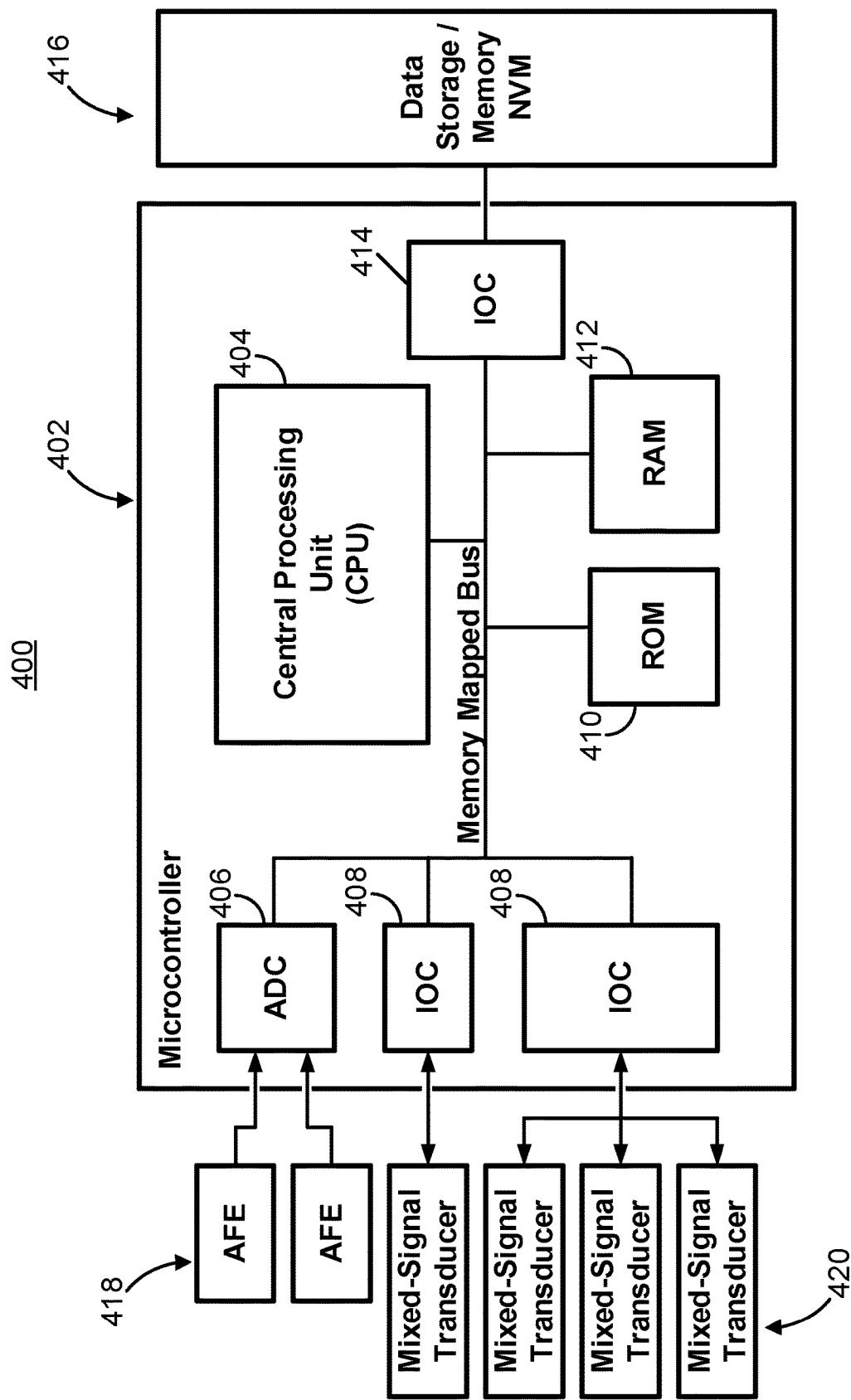
FIG. 4 shows an example of hardware that can be used to implement a portion of a remote monitor shown in FIG. 2 in accordance with some embodiments of the disclosed subject matter.

FIG. 4 shows an example 400 of hardware that can be used to implement a portion of remote monitor 102 of FIG. 2 in accordance with some embodiments of the disclosed subject matter. Remote physiological monitors are generally configured to be incorporated into a minimal form factor and to achieve low power usage over long run-times. These multiple constraints (which can, for example, limit the battery size) can require tradeoffs when designing a wearable device.

As shown in FIG. 4, a low-power remote monitor and recorder can include a microcontroller 402, which can include a processor 404, an analog-to-digital converter (ADC) 406, one or more I/O pins 408 (e.g., configured as interrupt on change (IOC) I/O pins), read only memory 410, random access memory 412, one or more pins 414 configured to connect MCU 402 to non-volatile memory 416. In some embodiments, MCU 402 can receive signals from one or more analog front ends (AFEs) 418 and/or mixed-signal transducers 420. In such embodiments, CPU 404 can use a program stored by ROM 410 to encode the signals using the mechanisms described herein, while temporarily storing signal values in RAM 412. In some embodiments, the k-ary tree can be stored in ROM 410, and or RAM 412 during operation. Note that although FIG. 4 is described as including CPU 404, this is merely an example, and any type of processor can be used to encode signals encode analog and/or digital physiological signals in a remote monitor. For example, FIG. 4 can be implemented using an FPGA or ASIC, in which one or more functions are performed by logic blocks or logic of the FPGA or ASIC that are configured to implement one or more components of a system for low-power encoding of continuous physiological signals in a remote physiological monitor. For example, an encoder component described below in connection with FIG. 5A can be implemented in logic of an FPGA or ASIC.

Figure 5A:
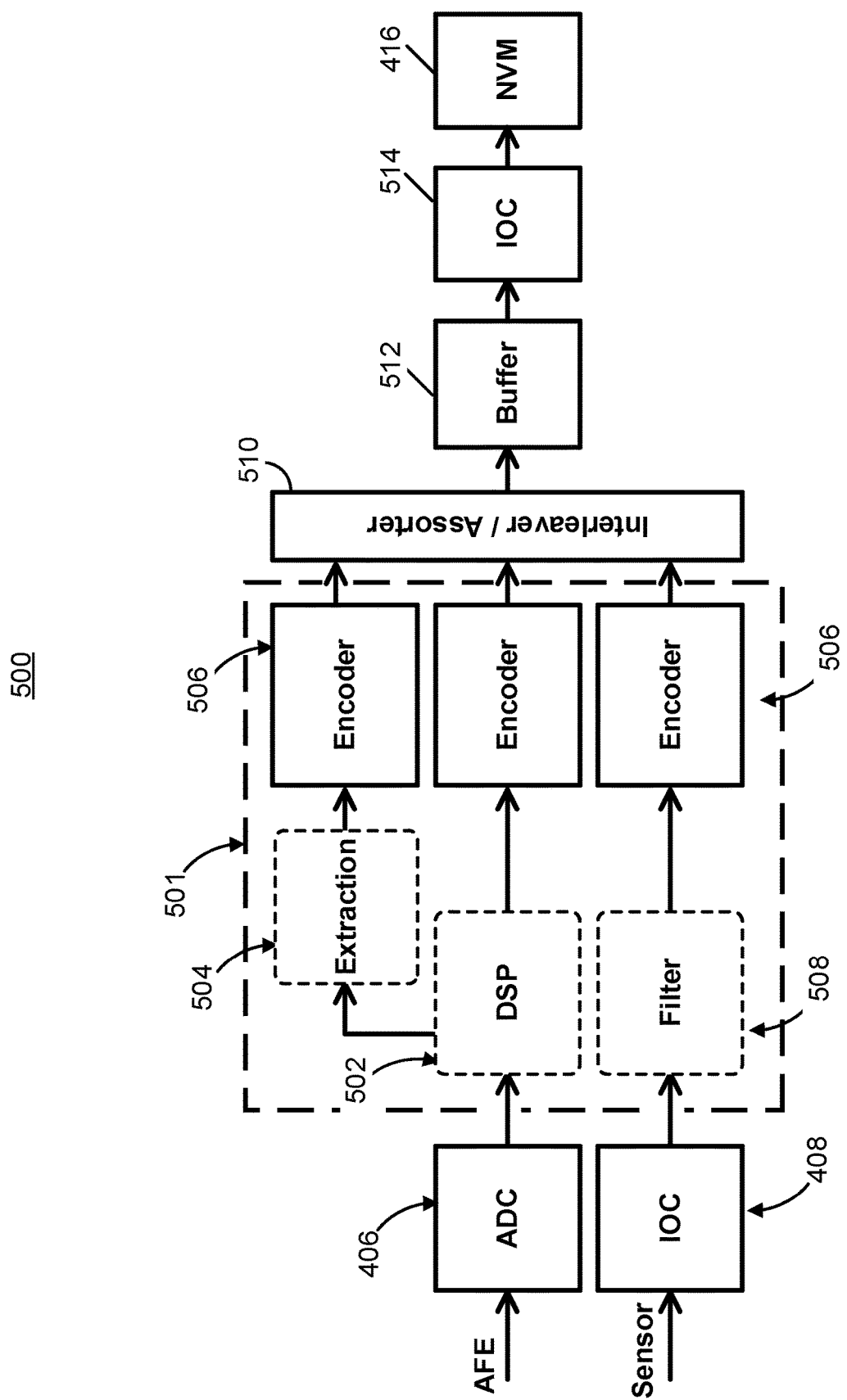
FIG. 5A shows an example of an information flow that can be used to encode analog and/or digital physiological signals in a remote monitor in accordance with some embodiments of the disclosed subject matter.

FIG. 5A shows an example 500 of components that can be used to encode analog and/or digital physiological signals in a remote monitor in accordance with some embodiments of the disclosed subject matter. As shown in FIG. 5A, a processor 501 (e.g., a CPU, FPGA, ASIC, etc.) can receive sensor data from one or more analog sensors via ADC 406. A digital signal from ADC 406 can be optionally be processed by a digital signal processor (DSP) 502, and in some cases, can be processed through a low overhead physiological information extractor 504. In some embodiments, when the extraction or smoothing and decimation is included, an additional (e.g., virtual) channel can be used to preserve both the processed and raw samples. In some embodiments, the converted signals can be received by an encoder 506, which can encode the signal using techniques described herein. Additionally, in some embodiments, a digital signal from IOC 408 can optionally be received by a filter 508, which can filter unwanted portions of the signal, and can pass the signals to encoder 506, which can encode the signal using techniques described herein. In some embodiments, encoders 506 can output the encoded signals to a buffer 512 (e.g., implemented using RAM 412) via an interleaver 510 (e.g., implemented using a time division multiplexer) for output to non-volatile memory 416 in blocks of bytes via one or more pins 414.

Figure 5B:
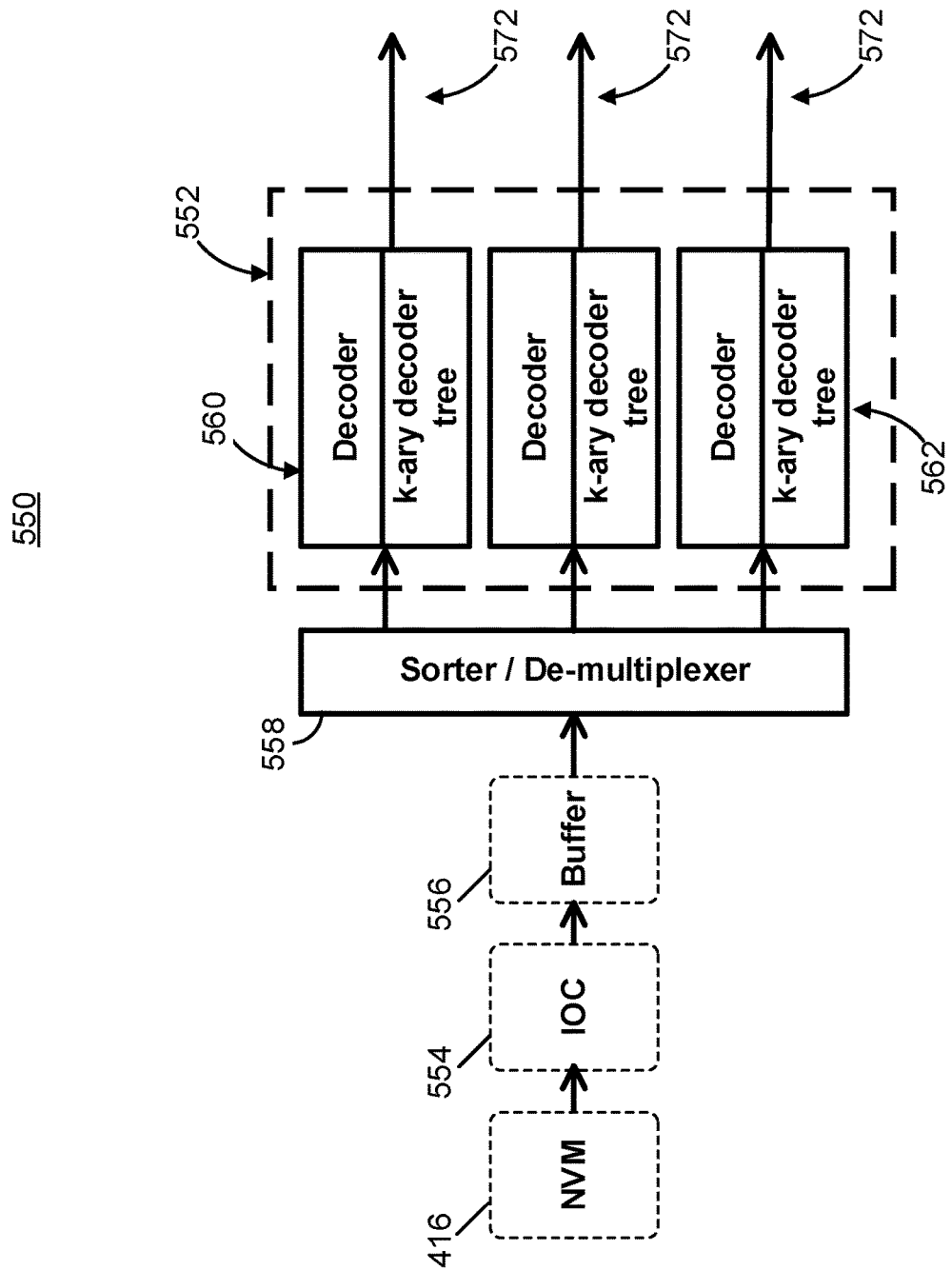
FIG. 5B shows an example of components that can be used to decode values of analog and/or digital physiological signals that were encoded by a remote monitor using techniques described herein in accordance with some embodiments of the disclosed subject matter.

FIG. 5B shows an example 550 of components that can be used to decode values of analog and/or digital physiological signals that were encoded by a remote monitor using techniques described herein in accordance with some embodiments of the disclosed subject matter. As shown in FIG. 5B, encoded values can be accessed by a processor 552 (e.g., a CPU, FPGA, ASIC, etc.) from a non-volatile memory (e.g., non-volatile memory 416) via one or more pins 554 and a buffer 556 (e.g., implemented via RAM) and a demultiplexer 558. In some embodiments, decoder 552 can include one or more decoder modules 560 to 562 which can each have a representation of a k-ary tree used to encode the values. For example, decoder 560 can be used do decode ECG signals that were encoded using a k-ary tree specific to ECG signals, while decoder 562 can be used to decode motion signals that were encoded using one or more k-ary trees specific to motion information (e.g., there can be separate k-ary trees for different axes of motion).

Figure 5C:
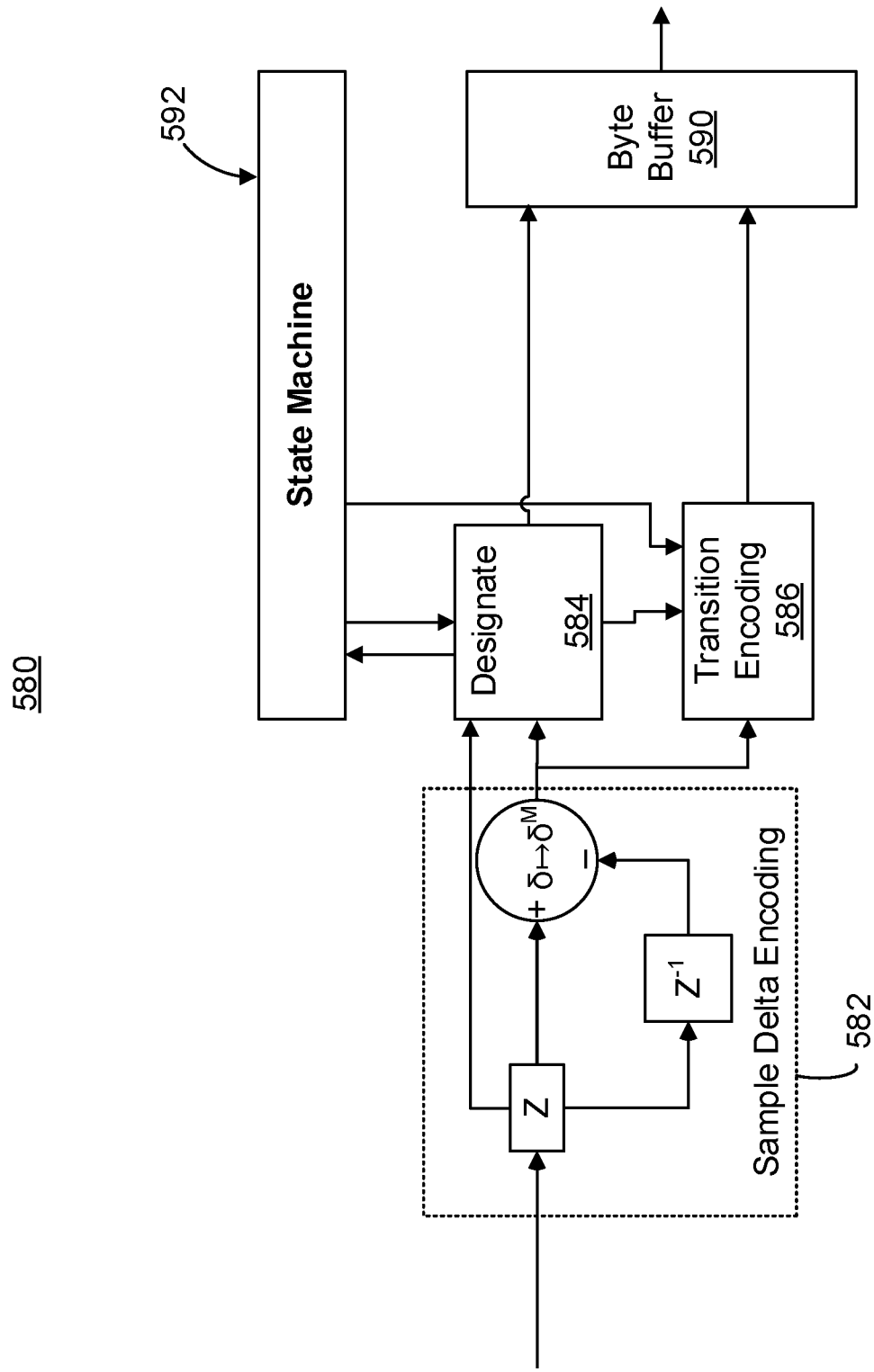
FIG. 5C shows an example of a hardware that can be implemented in a special purpose processor to encode analog and/or digital physiological signals in a remote monitor in accordance with some embodiments of the disclosed subject matter.

FIG. 5C shows an example 580 of a hardware that can be implemented in a special purpose processor to encode analog and/or digital physiological signals in a remote monitor in accordance with some embodiments of the disclosed subject matter. As shown in FIG. 5C, hardware 580 can include a sample delta encoding component 582 that can receive a first digital value (e.g., at time N) corresponding to a sample value, and a second digital value (e.g., at time N+1) corresponding to a next sample value. The previous (e.g., first) sample value can be delayed by one sample interval (e.g., as indicated by the $z^{-1}$ unit delay block), and subtracted from the current (e.g., second) sample value, and the difference (e.g., the delta) can be output from sample delta encoding component 582. Additionally, the current (e.g., second) sample value can also be output from sample delta encoding component 582 (e.g., for use in generating a sample token).

In some embodiments, hardware 580 can include a designation component 584 that can designate which of N token types the delta corresponds to, if any (e.g., the delta may not be encoded, as the sample may be encoded as a sample token). In some embodiments, designation component 584 can be implemented using up to N compare circuits. For example, as described below in connection with FIG. 7, designation component 584 can determine whether the delta is likely to correspond to a branch from a current node of a k-ary tree, and if, can determine whether the number of bits required to represent the delta is less than successively larger thresholds. In some embodiments, In some embodiments, hardware 580 can include a transition encoding component 586, which can implement hardware for encoding a sequence of deltas based on a k-ary tree that can be used based on which token type designation component 584 selects based on the value of the delta output from sample delta encoding component 582. For example, transition encoding component 586 can translate the delta to an unsigned transition (e.g., as described below in connection with FIG. 6B) which can involve flip, shift, and add logic circuits. As another example, transition encoding component 586 can calculate which node to move to at a next level of the k-ary tree, which can involve shift, add, and compare logic circuits. As yet another example, transition encoding component 586 can determine whether the transition encoding is to be terminated (e.g., if there is not corresponding node at the next level) or updated, which can involve compare and increment logic circuits. As still another example, transition encoding component 586 can encode the position of the node (e.g., based on the height and index of the node, as described below in connection with FIG. 6B) if the encoding is terminated, which can involve shift and mask logic circuits.

In some embodiments, hardware 580 can include a state machine 590, which can control operations of the circuitry. For example, state machine 590 can be configured to execute at least a portion of process 700 described below in connection with FIG. 7.

In some embodiments, hardware 580 can include a byte buffer 592 that can convert variable length bit width tokens into fixed eight bit outputs for storage and/or transmission, such that an encoded bit stream is output as a stream of bytes.

Figure 6A:
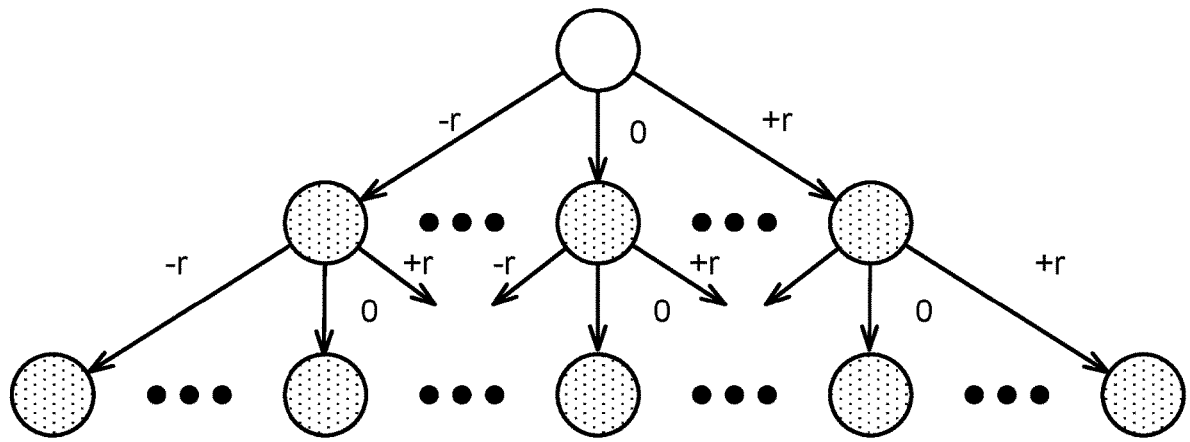
FIG. 6A shows an example of a delta k-ary tree that can be used to encode sequences of deltas between successive signals in accordance with some embodiments of the disclosed subject matter.

FIG. 6A shows an example 600 of a delta k-ary tree that can be used to encode sequences of deltas between successive signals in accordance with some embodiments of the disclosed subject matter. As shown in FIG. 6A, a delta stream can be represented using a k-ary tree, which can then be used to encode a particular sequence of deltas based on the position of the node representing the end of the sequence. In the tree shown in FIG. 6A, k is the maximum number of branches from each interior node. For example, for k=4, each node can have up to 4 branches representing deltas of −1, 0, 1, and 2. Note that, in general, delta values represented in the k-ary can be contiguous, and the same for each node (e.g., other than leaf nodes). However, delta values represented in the k-ary tree can be non-contiguous (e.g., a commonly occurring but non-contiguous delta can be included), and the deltas can be the same for each node. This can facilitate recognition of whether a current delta value is represented in the k-ary tree. Alternatively, in some embodiments, each of one or more nodes can be associated with a lookup table that can include a list of values associated with branches from the node. For example, a particular node can be associated with a lookup table that includes non-standard delta values (e.g., delta values that are not associated with each node), and may or may not include the standard delta values. In some embodiments, such a lookup table can also indicate whether the current node is a leaf node. As shown in FIG. 6A, each node in the tree can represent a unique sequence of delta transitions. The number of nodes in the tree is a function of k, the tree breadth, and the depth of the tree h (i.e., the number of levels in the tree). In some embodiments, because the position of the node represents a unique sequence, the position can be encoded in a bit-stream that represents the transitions. In some embodiments, when building a token for a node in the tree, the depth h and the node index $n_i$ can be used to identify the sequence delta transitions. Additionally or alternatively, in some embodiments, each node in the k-ary tree can correspond to a unique bit sequence, each sequence having a predetermined number of bits.

Figure 6B:
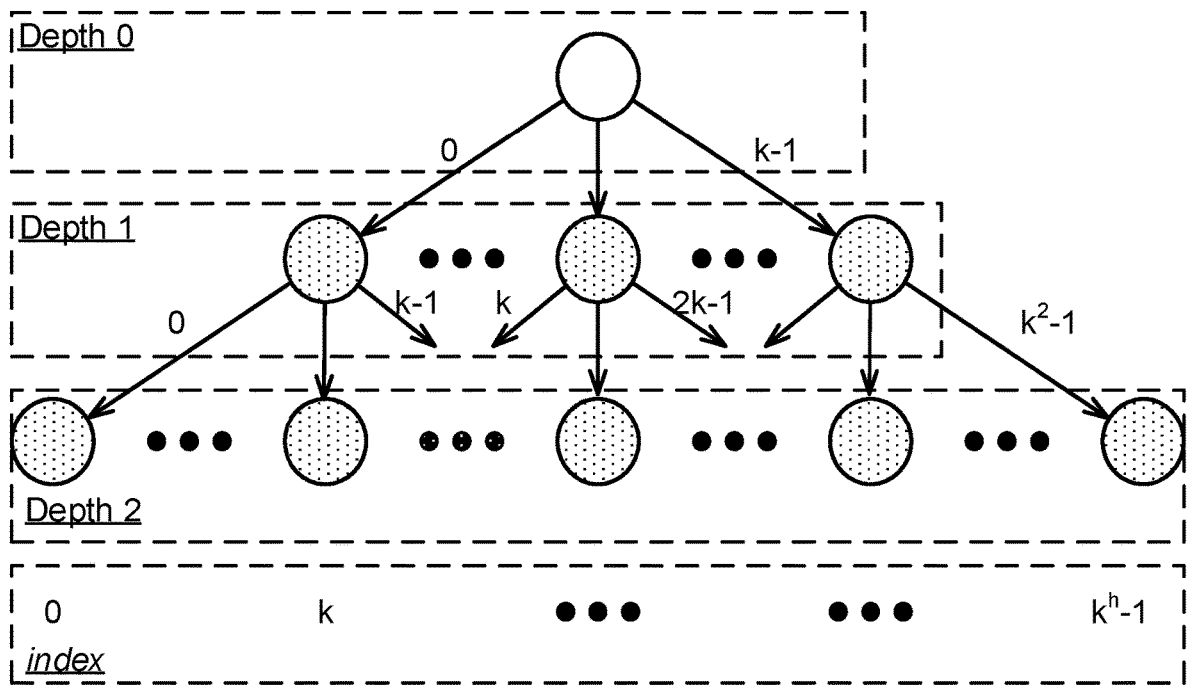
FIG. 6B shows an example of an unsigned delta k-ary tree that can be used to encode sequences of deltas between successive signals that have been mapped onto unsigned values in accordance with some embodiments of the disclosed subject matter.

FIG. 6B shows an example 610 of an unsigned delta k-ary tree that can be used to encode sequences of deltas between successive signals that have been mapped unsigned values in accordance with some embodiments of the disclosed subject matter. In some embodiments, the k-ary tree can be reconfigured based on a mapping of delta values to a set of unsigned values, such that the leftmost branch always corresponds to zero. As zero is often the most common delta value, this can result in tokens with decreased lengths, as the node index can generally be expected to be closer to the left of the tree, and accordingly can be encoded with fewer bits. In some embodiments, the $\delta_i$ can be calculated and then translated to facilitate low power encoding.

Let $\delta_1 = Val_1 - Val_{i-1}$ (1)

If $(\delta_1 \geq 0)$ (2)

Then $\delta_{i\_TX} = 2 \times \delta_i$ (3)

Else $\delta_{i\_TX} = -2 \times \delta + 1$ (4)

In some embodiments, the translated number can be a conversion of an absolute value comparison into a bit mask.

Unless otherwise limited, there are $k^h$ nodes at depth h, and both the depth h and node index $n_i$ need to be encoded. However, in some embodiments, node index can be limited to a specific maximum value at any individual level, as otherwise the number of bits required to represent the node index can cause diminishing advantage regarding the effective compression ratio. When the maximum node index is limited, the tree will generally be lop-sided to the left, and the actual number of nodes at any given depth will be limited by the maximum index. This cap on the node index can prevent large node values, so the tree will terminate once the maximum node index, $i_{max}$ is reached at a particular level. Note that the node index encoding described above was optimized for the leftmost nodes. In general, the structure of the k-ary tree (e.g., number of nodes at each level, branches from each node, delta values associated with branches, etc.) is generated prior to encoding of a signal using the tree. Additionally, the maximum bit lengths for fixed length tokens (e.g., as described below in connection with FIG. 6B), can be pre-selected.

In some embodiments, the next cursor coding in either a balanced or a lopsided k-ary tree can be calculated directly from the current cursor encoding, using only the maximum height and a list of the maximum numbers of nodes at each level of the tree. EQ. (5) shows an example of operations that can be used to produce a next height and index from a current k-ary node encoded as [height index] (the k-ary tree cursor), the new delta (e.g., $\delta_{NEW}$), and if the tree is unbalanced (e.g., as described below in connection with FIG. 6D), a table of [height($H_1$), bit shift ($S_1$), and bit mask ($M_1$)]. If the tree is balanced, shown in FIG. 6C described below, S and M are constants, with $M_{ALL}$ k−1, and $S_{ALL} = \log_2(k)$.

$$\begin{aligned} Index_{NEW} &= \delta_{NEW} + (Index_{CUR} \ll S_{CUR}) \\ Emit_{NEW} \text{ IF: } & (Index_{NEW} \text{ AND } M_{NEW}) \neq 0 \\ H_{CUR} &= 1 \\ Index_{CUR} &= 0 \\ \text{Restart using } & \delta_{NEW} \\ Emit_{NEW} \text{ IF: } & Height_{NEW} = Height_{MAX} \\ H_{CUR} &= 1 \\ Index_{CUR} &= 0 \\ Height_{NEW} &= 1 + Height_{CUR} \\ \text{Process next } & \delta \end{aligned} \quad (5)$$

Note that although encoding is generally described in connection with the translated numbers described of FIG. 6B, a similar flow can be used to convert untranslated numbers to a bit mask. In some embodiments, each successive level of height that is used can provide a higher compression ratio, and accordingly a potential increase in the number of nodes at successive levels may be useful. Accordingly, in some embodiments, the maximum number of nodes can vary from height value to height value, but the actual distribution of the nodes used in the tree may not favor this type of node index distribution, depending on the parameters and optimization.

Figure 6C:
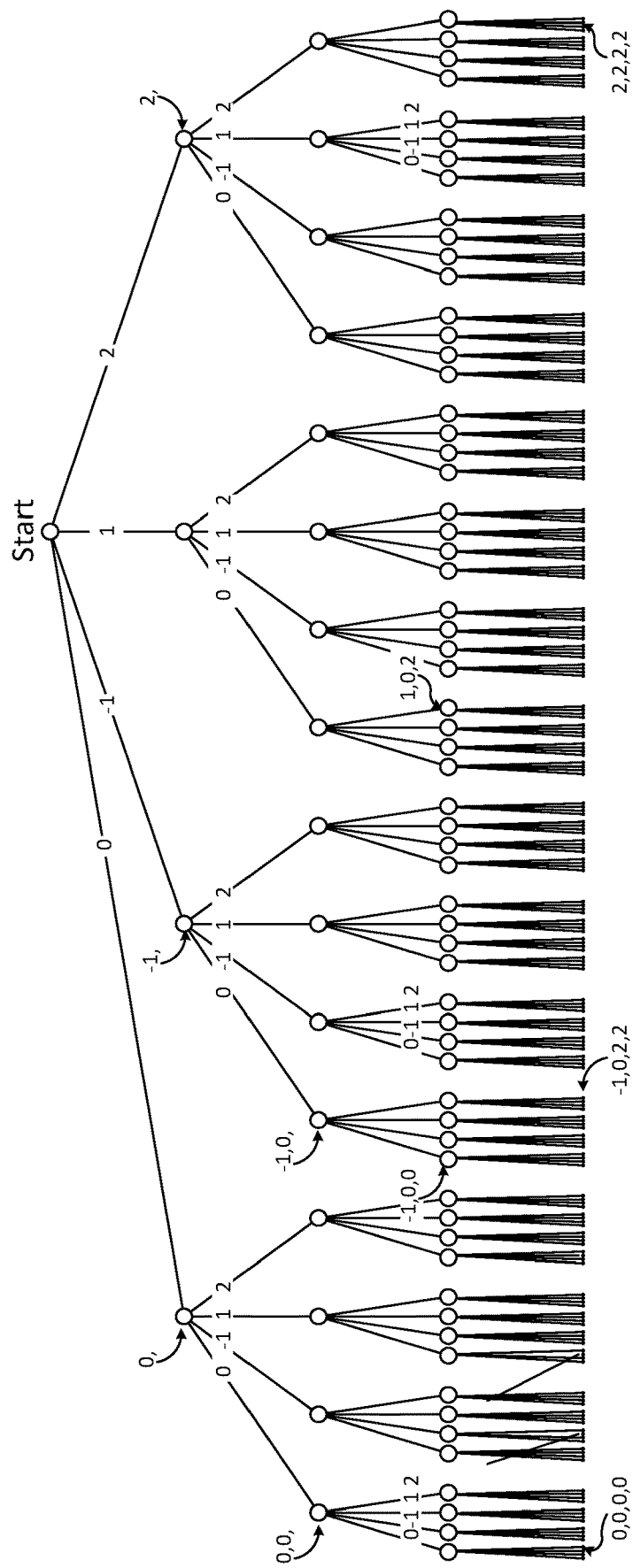
FIG. 6C shows an example of a balanced k-ary tree that can be used to encode sequences of deltas between successive signals in accordance with some embodiments of the disclosed subject matter.

FIG. 6C shows an example of a balanced k-ary tree that can be used to encode sequences of deltas between successive signals in accordance with some embodiments of the disclosed subject matter. As shown in FIG. 6C, each node represents a sequence of delta values, and each node at a particular level is associated with the same number of branches corresponding to the same delta values.

Figure 6D:
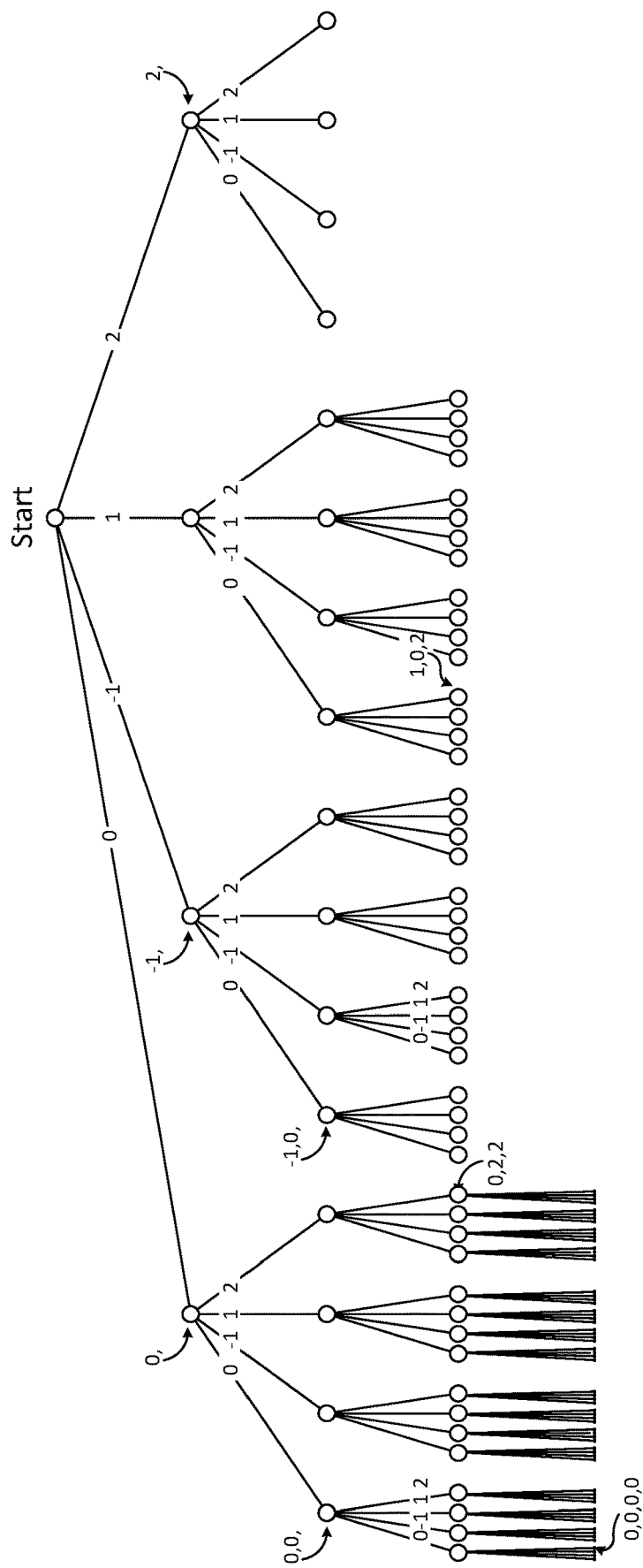
FIG. 6D shows an example of an unbalanced k-ary tree that can be used to encode sequences of deltas between successive signals in accordance with some embodiments of the disclosed subject matter.

FIG. 6D shows an example of an unbalanced k-ary tree that can be used to encode sequences of deltas between successive signals in accordance with some embodiments of the disclosed subject matter. As shown in FIG. 6D, each node represents a sequence of delta values, however, some nodes at a particular level can be associated with branches corresponding to the delta values, while other nodes in the same level can be leaf nodes.

Figure 6E:
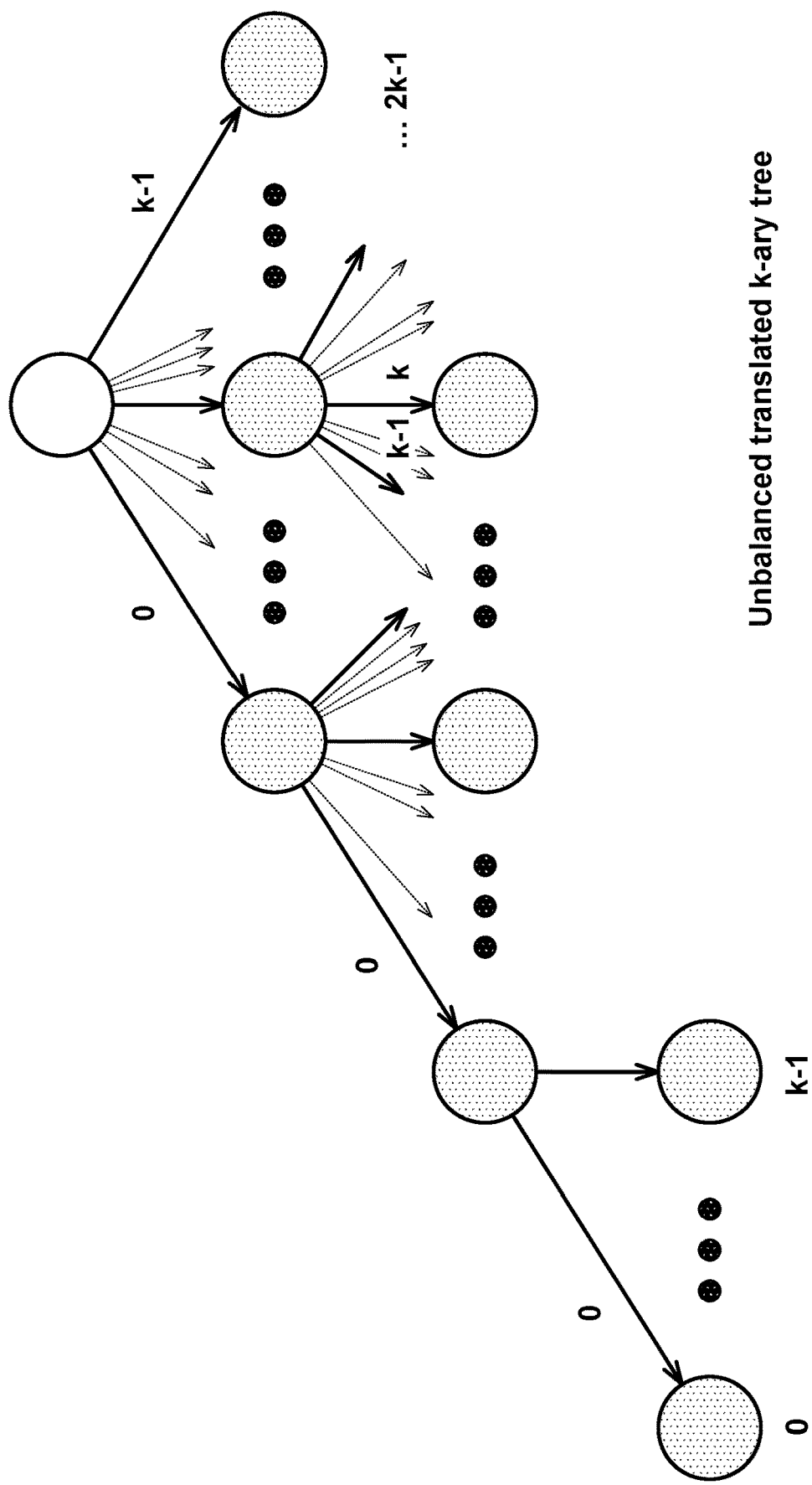
FIG. 6E shows an example of an unbalanced translated k-ary tree that can be used to encode sequences of deltas between successive signals in accordance with some embodiments of the disclosed subject matter.

FIG. 6E shows an example of an unbalanced translated k-ary tree that can be used to encode sequences of deltas between successive signals in accordance with some embodiments of the disclosed subject matter. As shown in FIG. 6E, each node represents a sequence of delta values, and certain nodes can include different numbers of branches (additional branches shown with dotted lines), which can be represented in a lookup table corresponding to the node.

Figure 7:
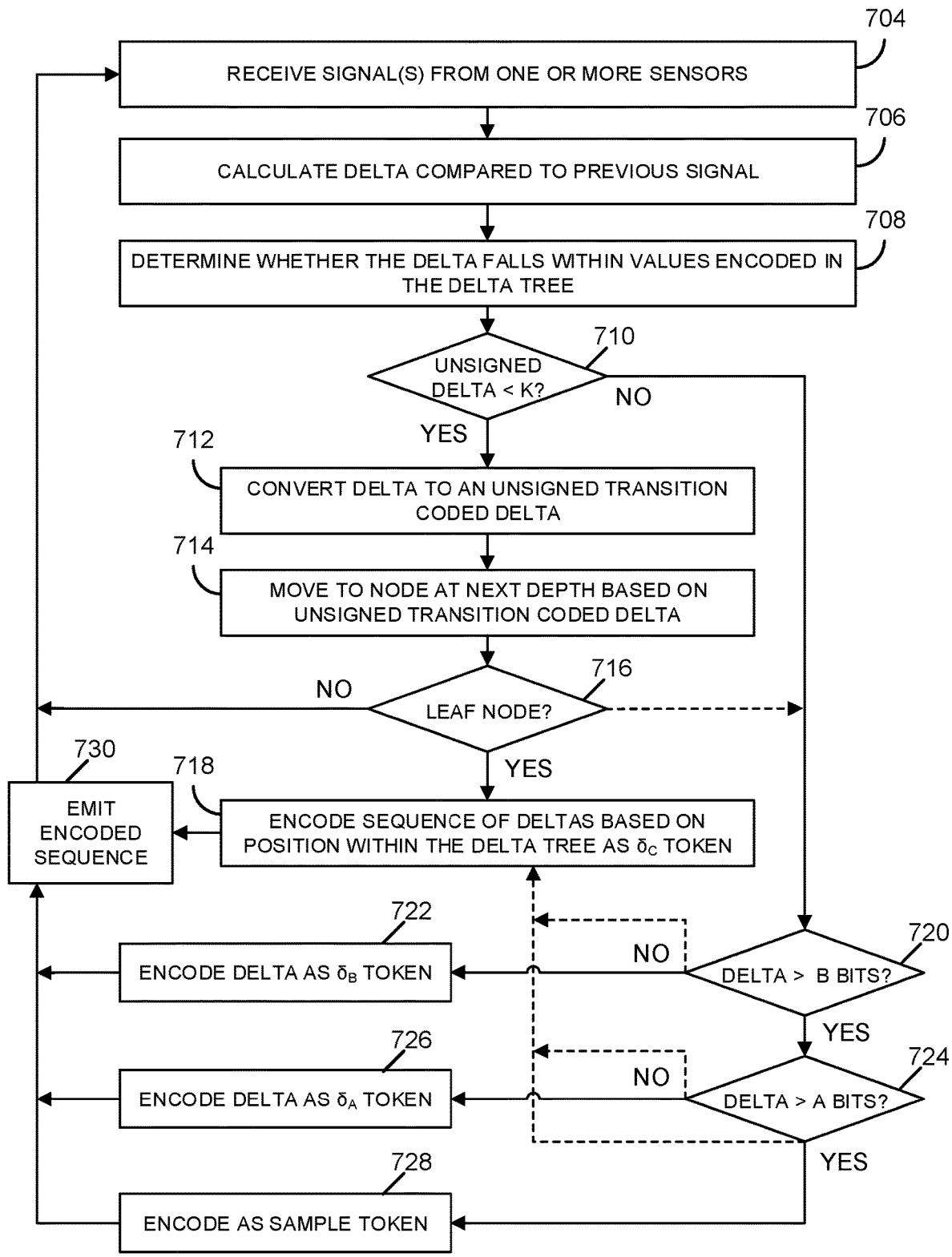
FIG. 7 shows an example of a process for low-power encoding of continuous physiological signals in a remote physiological monitor in accordance with some embodiments of the disclosed subject matter.

FIG. 7 shows an example 700 of a process for low-power encoding of continuous physiological signals in a remote physiological monitor in accordance with some embodiments of the disclosed subject matter. As shown in FIG. 7, at 704, process 700 can receive a signal from a sensor at a first time, and can store the second signal in memory (e.g., RAM, a cache, etc.).

At 706, process 700 can calculate a difference (i.e., delta) between the first signal and the second signal, which can include reading each of the signals, and a subtraction operation. Process 700 can store the delta in memory (e.g., RAM, a cache, etc.). In some embodiments, process 700 can translate the delta between the first signal and the second signal into an unsigned representation of the delta at 706. For example, as described above in connection with EQS. (1) to (4), and below in connection with EQ. (6), process 600 can perform one or more operations to map the calculated delta value to an unsigned representation of the delta value.

At 708, process 700 can determine whether the delta value is represented by a branch in the k-ary tree. For example, if the delta value is zero (e.g., for a tree similar to the tree shown in FIG. 6B), process 700 can determine that the delta is represented by a branch in the tree. As another example, if the unsigned representation of the delta is less than a predetermined value (e.g., k), process 700 can determine that there is a branch representing the delta (unless the current node is a leaf node). As yet another example, if the delta value based on the current height and index, and the maximum index of the next level of the k-ary tree, process 700 can determine that there is, or is not a branch, if the delta value based on whether a corresponding node in the next level would have an index that exceeds the maximum index for the next level of the tree. As still another example, process 700 can access a lookup table of delta values associated with branches from the current node, and can determine whether a node corresponding to the current delta exists by determining that the current delta is present in the lookup table. Additionally or alternatively, in some embodiments, process 700 can use the operations described above in connection with EQ. (5) to determine whether the delta value is represented by a branch.

If process 700 determines that the delta value is represented by a branch in the tree ("YES" at 710), process 700 can move to 712, and can convert the delta to an unsigned transition coded delta. As described above in connection with FIG. 6B, in some embodiments, the delta values represented by branches in the tree can be mapped to a set of unsigned values with the lower absolute values (e.g., −1 and 1, then −2 and 2, and so on). For example, in some embodiments, process 700 can calculate an unsigned value v using the following:

$$v = \begin{cases} 2 \times dx, & dx < 0 \\ -2 \times dx - 1, & dx < 0 \end{cases} \quad (6)$$

where dx is the delta value. In some embodiments, mapping the delta value to the unsigned set of values can include, for example, a flip operation, a shift operation, and/or an add operation. Note that 712 can occur prior to determining whether the current delta falls within values encoded in the delta tree (i.e., 712 can occur after 706 and prior to 708). Additionally or alternatively, in some embodiments, at 710, process 700 can determine that the most recent delta value is not represented in the k-ary tree. For example, process 700 can determine that no branches are present in the tree that correspond to the most recent delta. As another example, process 700 can determine that a current node does not have a branches corresponding to the most recent delta, even if the current node is not a leaf node. In such embodiments, process 700 can move to 714 to process the current (i.e., most recent delta), and can move to 730 to output a token representing the node in the k-ary tree corresponding to the sequence of deltas that occurred before the most recent delta that was not included in the tree. For example, process 700 can emit the current value of the cursor node from the current node, and can end k-ary tree processing and begin further processing of the most recent delta value (e.g., restarting from 712 with the cursor reset to 0, or reset the cursor to zero and proceed to 720). In such an example, the k-ary tree representation that has been determined from previous sample deltas can be output as the next data in the encoded stream, and the k-ary tree state can be set to an initial value.

At 714, process 700 can move to a node at a next depth based on the unsigned transition coded delta value generated at 712 (e.g., based on which branch the unsigned delta value corresponds to).

At 716, process 700 can determine whether the node that process 700 has moved to is a leaf node (i.e., there are no branches descending from the node). If process 700 determines that the node is not a leaf node ("NO" at 716), process 700 can return to 704 to receive another sample from the sensor. Otherwise, if process 700 determines that the node is a leaf node ("YES" at 716), process 700 can move to 718, and can encode a sequence of delta values represented by the position of the node by storing a delimiter and token $\delta_C$ based on the depth h and the node index $n_i$, and can move to 704 to receive another sample from the sensor. In some embodiments, the node index $n_i$ is a function of the previous node index, which can be represented as:

$$n_h = n_{h-1} k + v, \quad (7)$$

Note that if k is a power of two, all of the multiplications in EQS. (6) and (7) can be achieved by only using shift operations.

If process 700 determines, at 710, that the delta does not correspond to a branch in the tree ("NO" at 710), process 700 can move to 720 to determine whether the number of bits required to represent the delta is greater than the number of bits (B) that can be represented by the smaller fixed length token (e.g., $\delta_B$). For example, as described above, the $\delta_B$ token can be a 6 bit token, and process 700 can determine whether the delta value can be represented using 6 bits or less (e.g., by comparing the delta value to the largest number that can be represented using the 6 bits of the $\delta_B$ token).

If process 700 determines that the delta value does not require greater than B bits ("NO" at 720), process 700 can move to 722, and can encode the delta value as a $\delta_B$ token, and process 700 can return to 704 to receive another sample from the sensor. Note that, in some embodiments, process 700 can encode the delta value as an unsigned delta value as described above in connection with EQ. (6). Otherwise, if determines that the delta value requires greater than B bits ("YES" at 720), process 700 can move to 724.

At 724, process 700 can determine whether the number of bits required to represent the delta is greater than the number of bits (A) that can be represented by the larger fixed length token (e.g., $\delta_A$). For example, as described above, the $\delta_A$ token can be a 12 bit token, and process 700 can determine whether the delta value can be represented using 12 bits or less (e.g., by comparing the delta value to the largest number that can be represented using the 12 bits of the SC token). Note that, in some embodiments, process 700 can encode the delta value as an unsigned delta value as described above in connection with EQ. (6).

If process 700 determines that the delta value does not require greater than A bits ("NO" at 724), process 700 can move to 726, and can encode the delta value as a $\delta_A$ token, and process 700 can return to 704 to receive another sample from the sensor. Otherwise, if determines that the delta value requires greater than A bits ("YES" at 724), process 700 can move to 728.

At 728, process 700 can encode the sample as a sample token by storing the sample value with a delimited indicating that the token represents a sample value (e.g., rather than a delta token). After encoding the sample token at 728, process 700 can return to 704 to receive another sample from the sensor. Note that, in some embodiments, if a previous delta value was a value corresponding to a branch in the tree (e.g., in a previous iteration, process 700 determined moved to the node at the next depth at 714), at 722, 726, or 728, in addition to encoding the current delta, process 700 can also move to 718 to encode the previous sequence of deltas represented by the position of the node that process 700 moved to at 714 of the last iteration.

At 730, process 700 can output a token (e.g., a $\delta_A$, $\delta_B$, $\delta_C$, and/or sample token) for storage in memory. For example, when process 700 determines that a particular delta or sequence of deltas is to be encoded as a particular type of token, process 700 can, as described above in connection with FIG. 5A, process 500, output the token encoding the sample value, delta, or sequence of deltas to a buffer (e.g., via a multiplexer), which can be used to temporarily store values to be recorded until they can be saved to non-volatile memory in blocks of bytes. For example, in some embodiments, when a most recently processed delta corresponds to a $\delta_A$, $\delta_B$, or sample token, process 700 can saved that token after saving any 8c token that was pending when process 700 determined that the most recent delta could not be added to the sequence (e.g., as described above in connection with 720 and 724).

Note that although the mechanisms described herein are generally described using four token types (the $\delta_A$, $\delta_B$, $\delta_C$, and sample tokens) this is merely an example, and other combinations of tokens can be used. For example, in some embodiments, what are described as the $\delta_C$ and sample tokens can be used without using the $\delta_A$ and $\delta_B$ tokens. In such an example, if a most recent delta is not represented in the k-ary tree (e.g., based on a current node), the delta can be encoded as a sample token, and any sequence based on preceding deltas can be encoded as a $\delta_C$ token. As a more particular example, if only the $\delta_C$ and sample tokens are used, 720-726 can be omitted, and process 700 can move to 718 and 728 when process 700 determines that the most recent delta is not included in the k-ary tree (or otherwise cannot be included in a current sequence of deltas). Similarly, in some embodiments, the $\delta_A$ can be omitted, and the $\delta_B$, $\delta_C$, and sample tokens can be used.

Alternatively, in some embodiments, more tokens (e.g., in addition to the $\delta_A$, $\delta_B$, $\delta_C$, and sample tokens) can be used to encode deltas. For example, additional tokens $\delta_D$, $\delta_E$, ..., $\delta_n$ can be used, such that process 700 performs a sequence of comparisons (e.g., as described above in connection with 720 and 724) to widths corresponding to each token. As a more particular example, process 700 can successively compare the length required (in bits) to encode the most recent delta to the number of bits (Na) used to represent the each token $\delta n$ such that the sequence of comparisons is $\{N_B, N_C, \ldots, N_{MAX}\}$ with $\{N_B < N_C < \ldots < N_{MAX}\}$.

Figure 8:
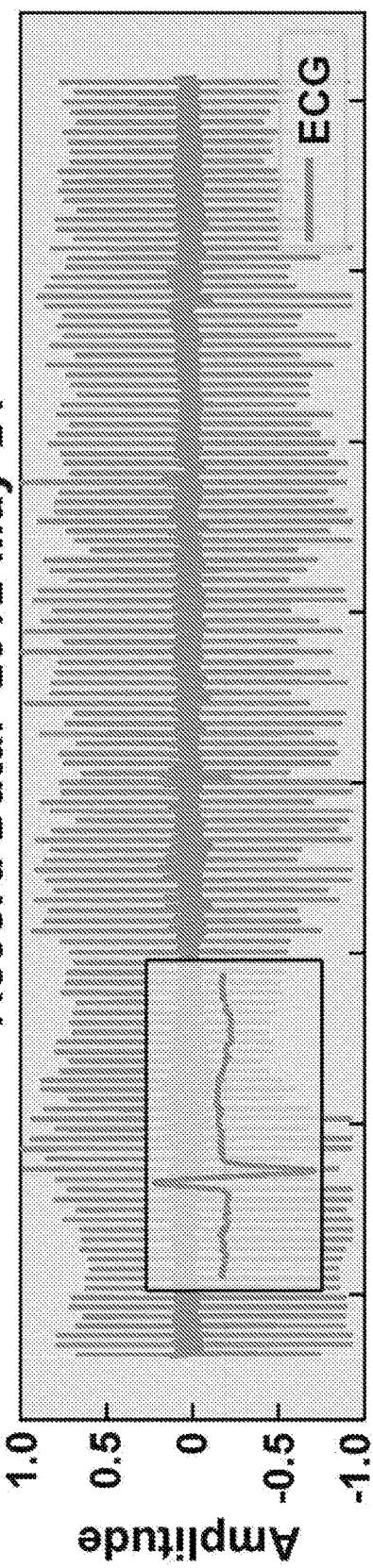
FIG. 8 shows an example of raw current data captured over time by a remote physiological monitor that can be encoded using techniques described herein for low-power encoding of continuous physiological signals in a remote physiological monitor.
Figure 8:
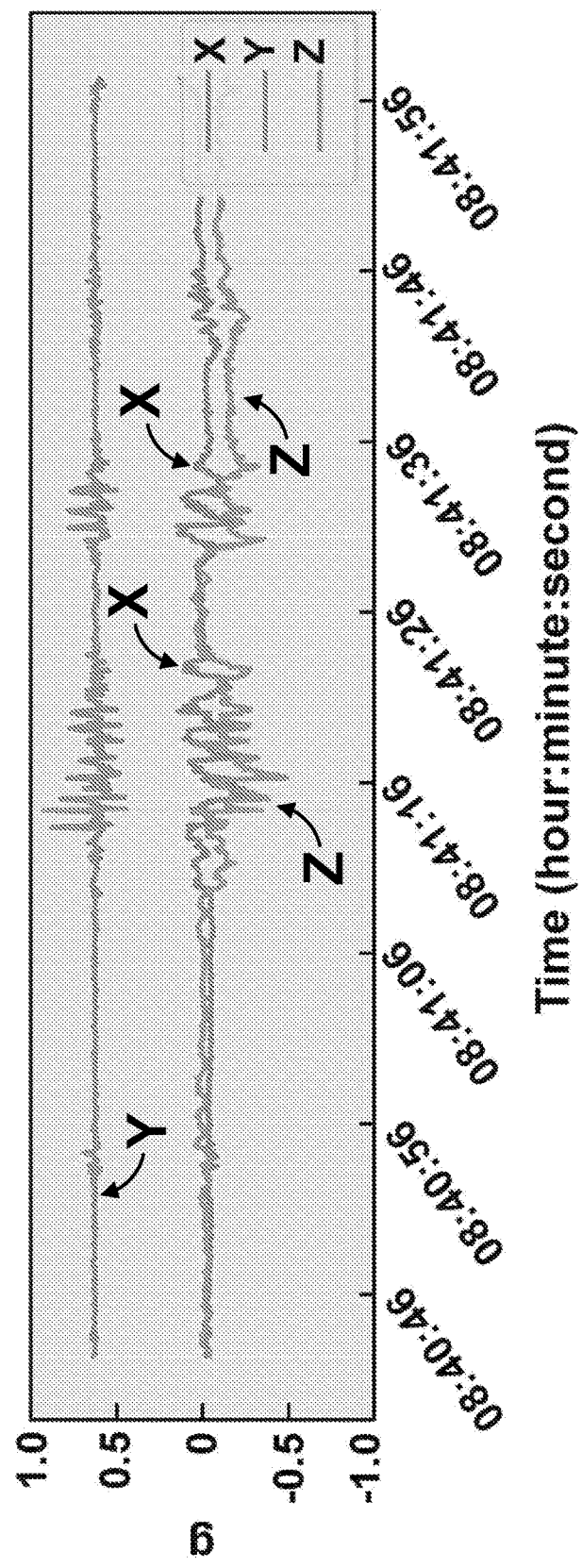

FIG. 8 shows an example of raw data captured by a remote physiological monitor that can be encoded using techniques described herein for low-power encoding of continuous physiological signals in a remote physiological monitor. Note that the units in FIG. 8 are normalized based on the potential outputs of the sensors. More particularly, FIG. 8 shows about 90 seconds of raw ECG and accelerometer signals collected by a remote monitor carried by an Elite climber three days into the final summit climb of Mount Everest. ECG is plotted as normalized amplitude (amplitude), and motion data is depicted in standard gravitational acceleration (g).

Figure 9:
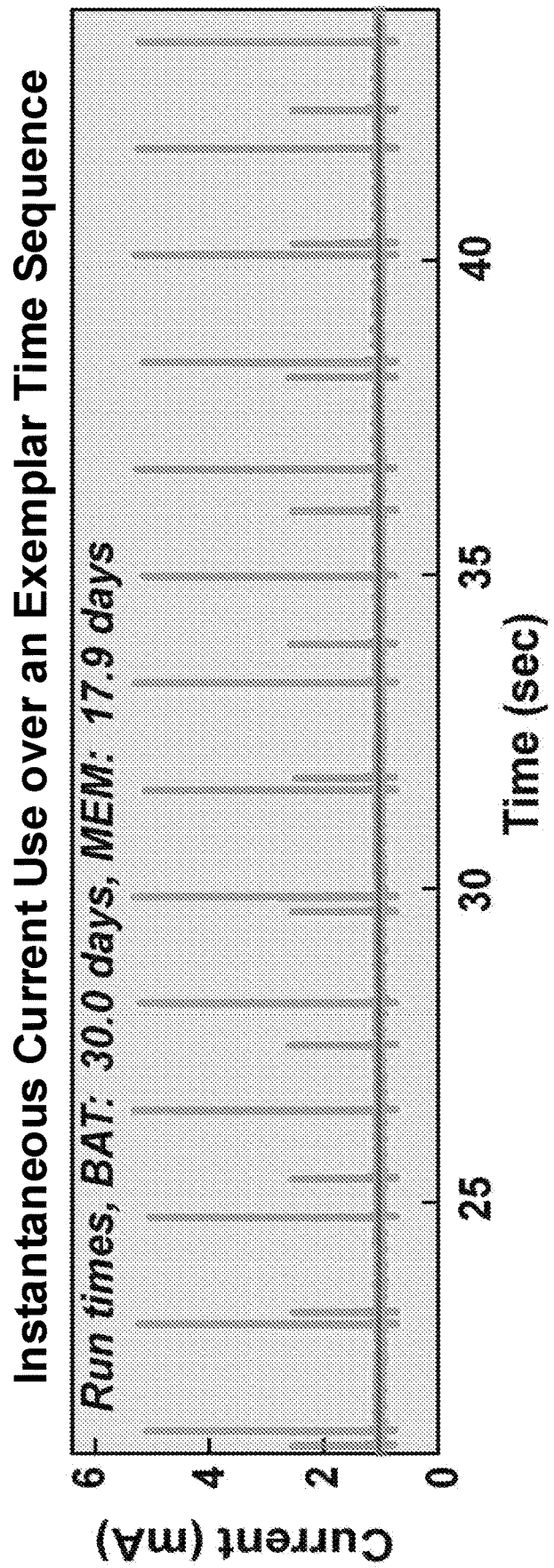
FIG. 9 shows an example of current levels measured from a remote physiological monitor that is encoding a physiological signal and writing the encoded signal to non-volatile memory using conventional techniques.

FIG. 9 shows an example of current levels of a remote physiological monitor that is encoding a physiological signal and writing the encoded signal to non-volatile memory using conventional techniques. In the example described above in which the Everest devices were used to collect data from climbers attempting to climb at least a portion of Mount Everest the devices were designed and configured (e.g. the number of sensor channels and sample rates) for low NVM power overhead, and the difference between the average current (including NVM writes) and the average low current (excluding NVM writes) is minimal. Similarly, as shown in FIG. 9, reducing the NVM write power had little effect on the overall system power consumption, whereas in other devices the overall NVM power may be much higher.

While the energy consumption impact of the encoding has not been directly measured, it is estimated that the impact will be minimal. For example, the encoding described above in connection with FIG. 7 can use 16 or fewer instructions to encode a sample. In a more particular example, an MSP430 microcontroller (available from TEXAS INSTRUMENTS), can use an average of three clock cycles per instruction. Accordingly, at operating frequency of 8 MHz, the encoding can be estimated to require 6 microseconds (μs) of additional processing time per sample. This estimated instruction execution time can be translated into an energy usage estimate by determining the percent increase. Given the Mount Everest configuration as a reference, roughly 50% of the time between samples is used to configure the hardware and save the sample, which amounts to roughly 1 millisecond (ms) of execution time. In this case, the additional 6 μs of estimated processing time is a negligible (i.e., less than a 1%) increase of execution time. The mechanisms described herein can consume minimal cycles to compute the encoding for the samples, and does not require the complete statistics for the data being encoded (e.g., as opposed to other encoding schemes, such as Huffman coding), thereby permitting real-time embedded encoding.

Figure 10:
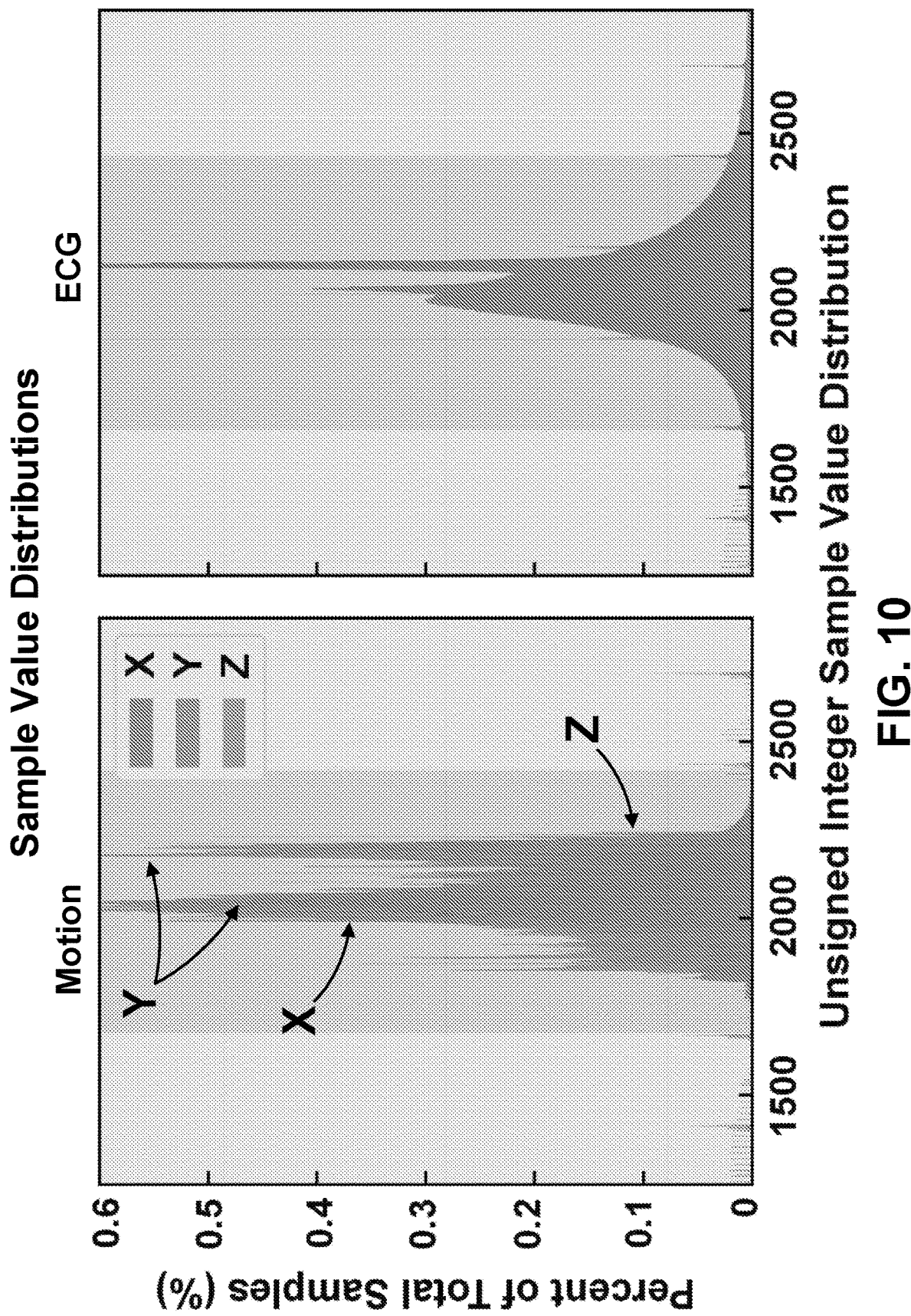
FIG. 10 shows an example distribution of how often various current level values appeared in the example data set shown in FIG. 8.

FIG. 10 shows an example distribution of how often various current level values appeared in the example data set shown in FIG. 8. In the example shown in FIG. 10, each of the vertical bars represents the percentage of the total example data set that has that value. These unsigned, raw, motion and ECG samples were captured by a remote physiological monitor, and can be encoded using techniques described herein. More particularly, FIG. 10 shows the distribution of more than 16 GB of raw 12-bit ECG and motion (accelerometer) data that was recorded during the Mount Everest expedition. The distribution shown is of the collected raw unsigned (unipolar) integer samples. That is, each sample of data was recorded as a 12-bit value mapped onto the scale of values output by the sensors. For example, as shown in FIG. 8, the ECG leads generally produce values centered around zero, and these can be mapped to 12-bit values by mapping zero to a value about halfway between zero and 4,095 (i.e., the maximum value that can be represented using 12 bits). Note that, in some embodiments, the mapping can be to a conventional binary ordering, or to any other suitable type of binary ordering, such as a Gray code ordering. The shaded bands in FIG. 10 shows the bins which contain 95% of the data on both sides of the mean data value. Note that the sample distribution in FIG. 10 includes all of the data collected, including times when ECG leads were off, during calibration tests, etc.

Figure 11:
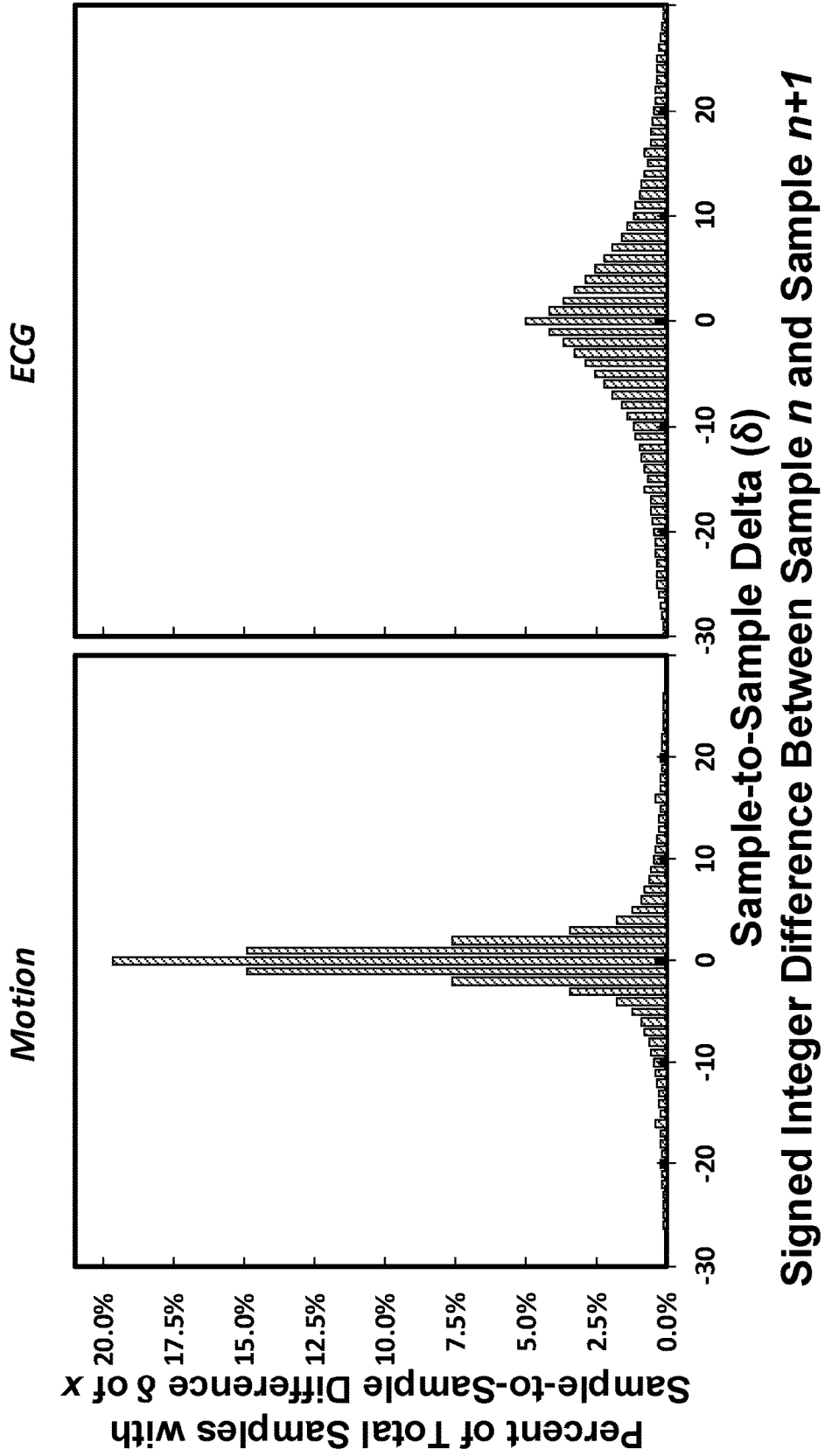
FIG. 11 shows an example distribution of deltas representing changes between successive samples of raw motion and ECG data captured by a remote physiological monitor.

FIG. 11 shows an example distribution of deltas representing changes between successive samples of raw motion and ECG data captured by a remote physiological monitor. More particularly, FIG. 11 shows the first difference of the data (i.e., the delta distribution) for the accelerometer and ECG data shown in FIG. 10, and is significantly more compact than the original data. For example, for the delta distribution shown in FIG. 11, 95% of the motion data is located in the central most 368 bins. Similarly, for the delta distribution shown in FIG. 11, 95% of the ECG data is located in the 385 central bins. As demonstrated in FIG. 11, the delta difference between sequential samples is typically small. Accordingly, much of the acquired data can be encoded using the difference between samples (sometimes referred to as delta encoding). More particularly, the delta distributions demonstrate that more than 70% of the motion data is included in the middle seven bins, and more than 45% of the ECG data is included in the middle 14 bins. Given that a delta value of zero is the most prevalent delta in these data sets, the occurrence of run-lengths was also calculated to determine if the use of run-length encoding would improve data compression, as described below in connection with FIG. 12.

Figure 12:
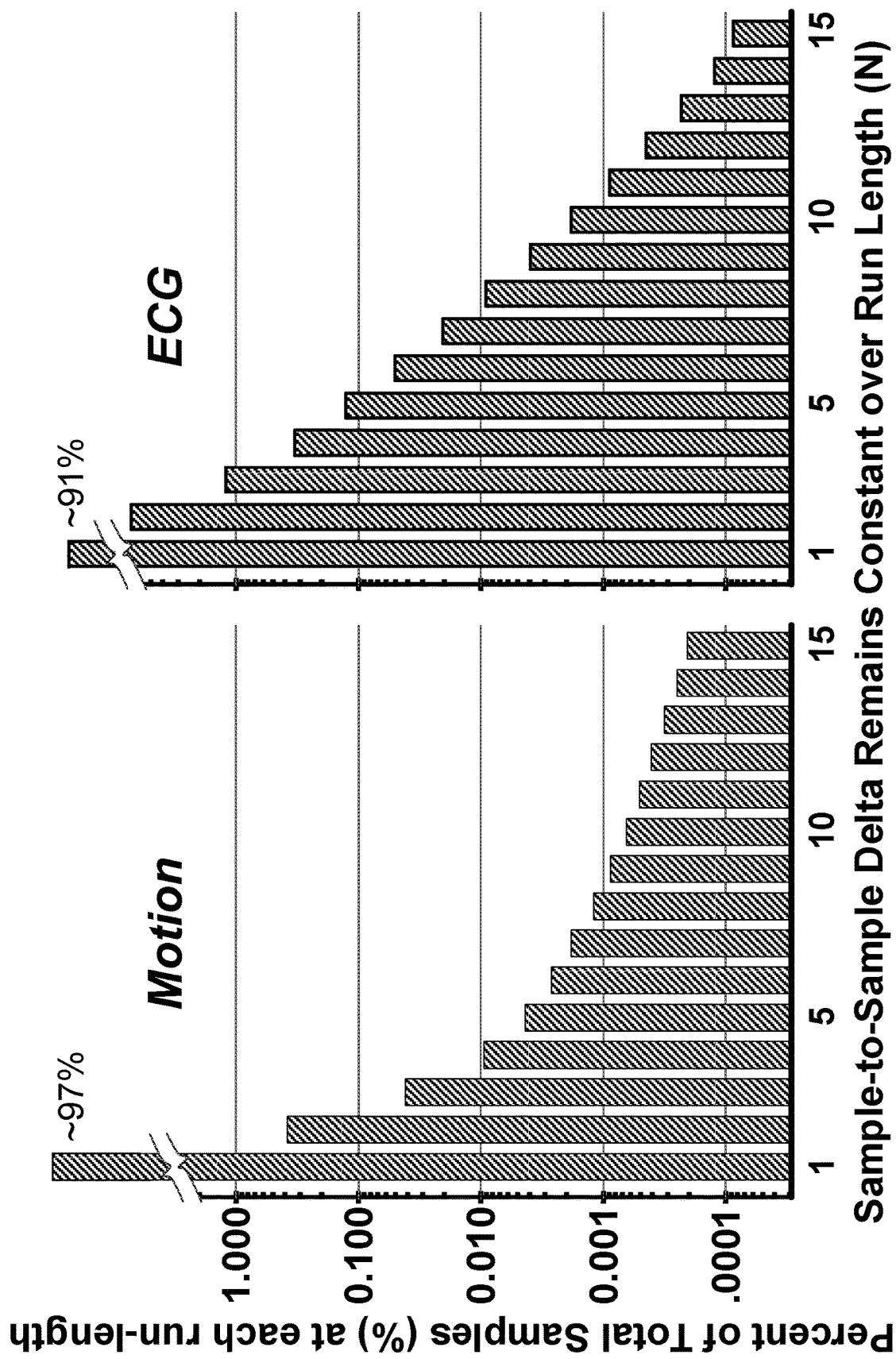
FIG. 12 shows an example distribution of run lengths in sequences of deltas representing changes between successive samples of raw motion and ECG data captured by a remote physiological monitor.

FIG. 12 shows an example distribution of run lengths in sequences of deltas representing changes between successive samples of raw motion and ECG data captured by a remote physiological monitor. As shown in FIG. 12, the run-lengths of calculated motion and ECG deltas for the Mount Everest data, where the majority of the data is useful motion and ECG data, does not often maintain a constant value (e.g., run lengths of 5 account for about 0.1% of the total data for motion, and 0.01% for ECG). Accordingly, using delta run-length is unlikely to yield more than limited gains.

Figure 13:
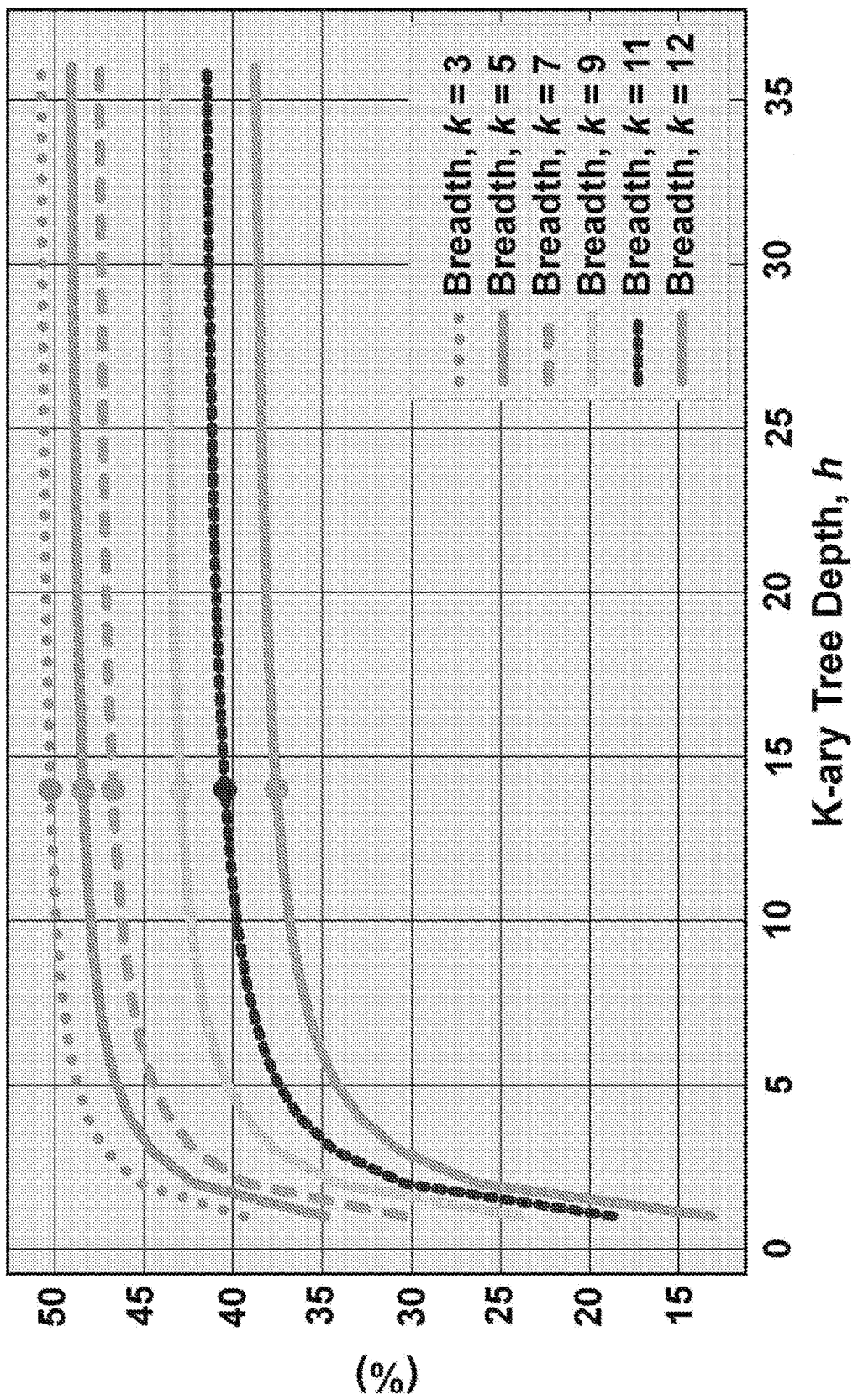
FIG. 13 shows an example of estimated data reductions that can be realized for various tree architectures using techniques described herein.

FIG. 13 shows an example of estimated data reductions that can be realized for various tree architectures using techniques described herein. More particularly, FIG. 13 shows an estimate of the reduction rate as a function of the tree breadth, k, and tree depth, h realized for a data set with one million samples. As shown in FIG. 13, at a given depth h, data reduction generally diminishes with increases in breadth.

Figure 14:
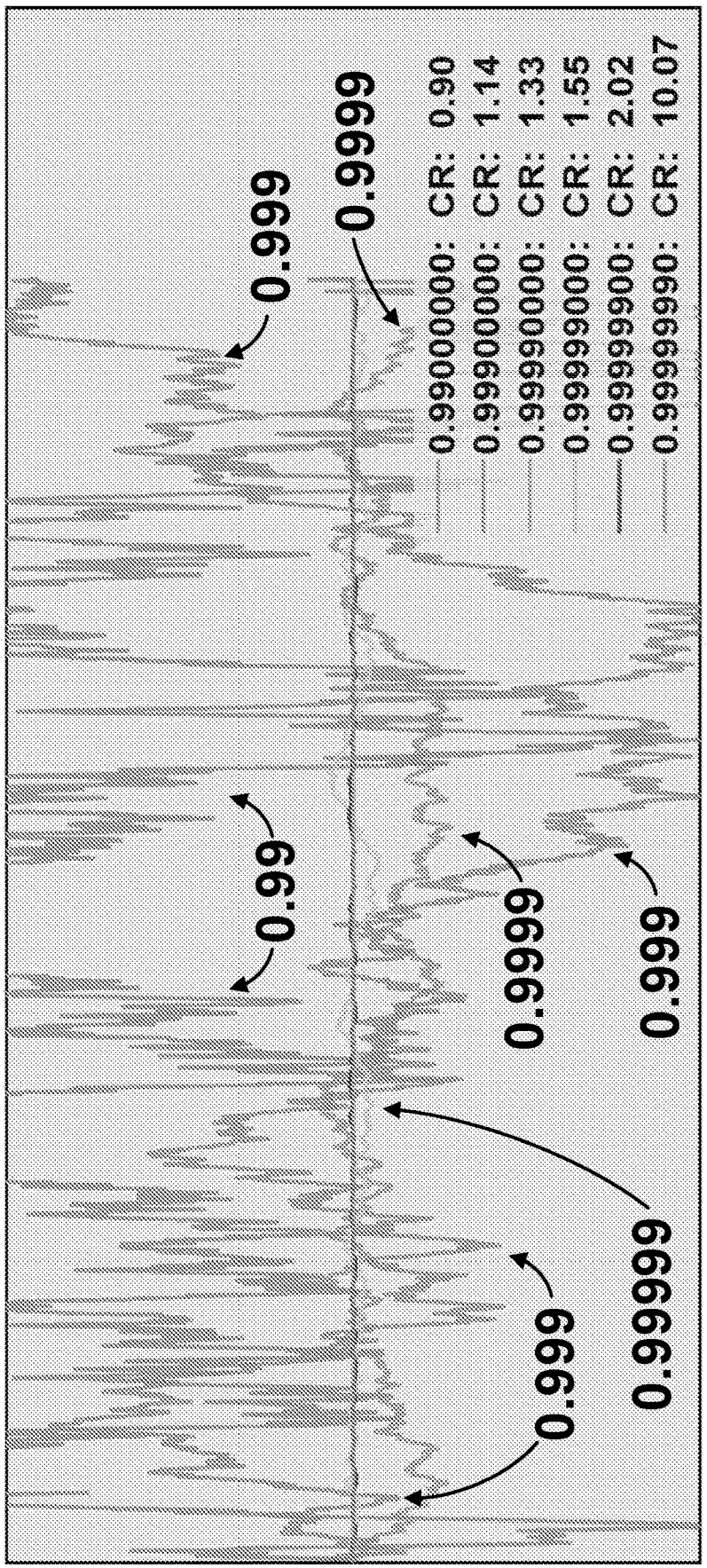
FIG. 14 shows an example of compression ratios realized by applying techniques described herein.

FIG. 14 shows an example of compression ratios realized by applying techniques described herein. As shown in FIG. 14, as the covariance of the contrived signals increases, the compression ratio (CR) also generally increases. Accordingly, using the techniques described herein can provide better power and storage savings for high covariance data. As shown in FIGS. 10 and 11, motion and ECG samples collected during the Mount Everest expedition generally have a high covariance with adjacent symbols. The compression ratio achieved by a particular encoding scheme can be represented as:

$$CR = \frac{\text{non-encoded number of bits}}{\text{encoded number of bits}}, \quad (8)$$

Note that while some lossy compression techniques have demonstrated impressive compression ratios with low weighted diagnostic distortion (WDD) and percentage root mean square difference (PRD), these techniques require substantial amounts of calculations to compress the data. For example, the technique described in Hamilton et al. ("Compression of the Ambulatory ECG by Average Beat Subtraction and Residual Differencing," IEEE Transactions on Biomedical Engineering, vol. 38, no. 3, pp. 253-259, March 1991) uses QRS extraction to reduce the data. However, even with efficient QRS extraction, the increase in energy consumption is enough that the benefits from the compression encoding (e.g., power savings when writing the compressed data to NVM over writing the raw signals to NVM) is offset by the increase in energy consumption due to the additional calculations required for a body-worn ambulatory device.

FIG. 15 shows a first table of compression ratios and data reductions realized by applying techniques described herein to encode data collected by various remote physiological monitors while subjects attempted to climb Mount Everest; a second table of compression ratios and data reductions realized by applying techniques described herein to encode ECG data collected from various subjects; and a third table comparing compression ratios of various conventional encoding schemes, and the techniques described herein for low-power encoding of continuous physiological signals in a remote physiological monitor.

Using techniques described herein, based on the achieved compression ratios for the Mt. Everest data, device runtime would have roughly doubled from two to four weeks of continuous recording. Additionally, although not described in detail herein, the techniques described herein also can reduce power consumption due to transmission of the data wirelessly in real time, as the total transmission power and energy scales with the amount of data being transmitted, and would consequently be reduced by an amount related to the compression ratio.

Techniques described herein were implemented and run against the recorded raw Mount Everest data, as well as against the MIT-BIH database.

TABLE I shows the compression ratios (CR) for a subset of devices that were used to monitor the climbers who summited Mount Everest. In addition to the CR, TABLE I also presents the reduction rate as a percentage, in which a reduction rate of 100% would result in no post-compression data remaining. The resulting size or bit rate after encoding is B (100 rdx), where B is the number of bits or bytes encoded, and rdx is the reduction rate.

TABLE II shows the CRs and reduction ratios as percentages for a subset of the records from the MIT-BIH database. Including the lowest and highest CR encodings, an average 1.72 CR was obtained across all MIT-BIH data records.

Note that, as shown in TABLE III, the compression results using techniques described herein are relatively modest by comparison with other published approaches. However, the compression ratios that are achieved are realized with minimal computational costs. TABLE III shows a CR comparison with other lossless encoding techniques. Note that the previous publications from which the CRs have been gather do not provide sufficient or consistent analysis to make a useful complexity or energy usage comparison. Note that other lossless encoders report similar CR ranges (e.g., 1.66-3.07). However, other encoding techniques often require considerably more resources. For example, for the DPCM predictor a dedicated integrated circuit was used to execute the encoding, requiring substantial design and fabrication costs. Some other encoders are intended to be integrated into analog-to-digital converters, however these techniques are not feasible when using many of the micro electro-mechanical system sensors that provide digital outputs.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the process of FIG. 7 can be executed or performed in any order or sequence not limited to the order and sequence shown and described in the figures. Also, some of the above steps of the process of FIG. 7 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

The invention claimed is:

1. A system for low-power encoding of continuous physiological signals, the system comprising:
a sensor; and
a remote physiological monitor comprising:
 a battery;
 memory storing a k-ary tree, the k-ary tree including a root node with k branches corresponding to k delta values, k nodes at a first depth below the root node each having k branches corresponding to the k delta values, and $k^2$ nodes at a second depth below the root node each having k branches corresponding to the k delta values, wherein the nodes at each depth are indexed such that each node is associated with an index number indicating that node's lateral position within that depth of the k-ary tree, and k>2;
 a processor coupled to the sensor, the processor programmed to:
 receive a first signal from the sensor at a first time, the first signal corresponding to a first sample value;
 receive a second signal from the sensor at a second time, the second signal corresponding to a second sample value;
 calculate a difference between the second sample value and the first sample value, the difference corresponding to a first delta value;
 determine that the first delta value corresponds to a first particular delta value of the k delta values;
 in response to determining that the first delta value corresponds to the first particular delta value, store a first depth and a first node index of a child node at the end of the branch corresponding to the first particular delta value;
 receive a third signal from the sensor at a third time, the third signal corresponding to a third sample value;
 calculate a difference between the third sample value and the second sample value, the difference corresponding to a second delta value;
 determine that the second delta value corresponds to a second particular delta value of the k delta values;
 in response to determining that the second delta value corresponds to the second particular delta value, store a second depth and a second node index of a child node at the end of the branch corresponding to the second particular delta value; and
 encode the sequence of the first delta value and the second delta value based on the second depth and the second node index.

2. The system of claim 1, wherein the sensor comprises an electrocardiogram lead, and the first signal is an analog signal.

3. The system of claim 1, wherein the sensor comprises an accelerometer, and the first signal is a digital signal.

4. The system of claim 1, wherein the processor is further programmed to:
receive a fourth signal from the sensor at a fourth time, the fourth signal corresponding to a fourth sample value;
calculate a difference between the fourth sample value and the third sample value, the difference corresponding to a third delta value; and
determine that the third delta value does not correspond to any of the k delta values.

5. The system of claim 4, wherein the processor is further programmed to:
encode the sequence of the first delta value and the second delta value in response to the determination that the third delta value does not correspond any of the k delta values.

6. The system of claim 4, wherein the processor is further programmed to:
determine that the node at the second depth and the second node index does not have any branches; and
in response to determining that the node at the second depth and the second node index does not have any branches, encode the sequence of the first delta value and the second delta value.

7. The system of claim 4, wherein the processor is further programmed to:
in response to determining that the third delta value does not correspond to any of the k delta values, compare the minimum number of bits required to represent the third delta value to a first number of bits of a first fixed bit length token $\delta_B$ to determine whether the minimum number of bits is greater than the first number of bits.

8. The system of claim 1, wherein the processor comprises an application-specific integrated circuit (ASIC).

9. A method for choosing the branch values for a k-ary tree, comprising:
obtaining a statistically significant sample of an input stream to be encoded;

encoding the input stream using a first set of k-ary branch values;

encoding the input stream using a second set of k-ary branch values;

determining that an amount of energy used to encode the input stream using the first set of k-ary values is lower than an amount of energy used to encode the input stream using the second set of k-ary values;

selecting the first set of k-ary branch values based at least in part on the determination that the amount of energy used to encode the input stream using the first set of k-ary values is lower than the amount of energy used to encode the input stream using the second set of k-ary values; and constructing a k-ary tree based on the first set of k-ary branch values for use in an encoder of a physiological monitoring system.

10. A method for low-power encoding of continuous physiological signals, the method comprising:

receiving a first signal from a sensor at a first time, the first signal corresponding to a first sample value;

receiving a second signal from the sensor at a second time, the second signal corresponding to a second sample value;

calculating a difference between the second sample value and the first sample value, the difference corresponding to a first delta value;

determining that the first delta value corresponds to a first particular delta value of k delta values of a k-ary tree, the k-ary tree including a root node with k branches corresponding to k delta values, k nodes at a first depth below the root node each having k branches corresponding to the k delta values, and $k^2$ nodes at a second depth below the root node each having k branches corresponding to the k delta values, wherein the nodes at each depth are indexed such that each node is associated with an index number indicating that node's lateral position within that depth of the k-ary tree, and k>2;

in response to determining that the first delta value corresponds to the first particular delta value, storing a first depth and a first node index of a child node at the end of the branch corresponding to the first particular delta value;

receiving a third signal from the sensor at a third time, the third signal corresponding to a third sample value;

calculating a difference between the third sample value and the second sample value, the difference corresponding to a second delta value;

determining that the second delta value corresponds to a second particular delta value of the k delta values;

in response to determining that the second delta value corresponds to the second particular delta value, storing a second depth and a second node index of a child node at the end of the branch corresponding to the second particular delta value; and encoding the sequence of the first delta value and the second delta value based on the second depth and the second node index.

11. The method of claim 10, wherein the sensor comprises an electrocardiogram lead, and the first signal is an analog signal.

12. The method of claim 10, wherein the sensor comprises an accelerometer, and the first signal is a digital signal.

13. The method of claim 10, further comprising:

receiving a fourth signal from the sensor at a fourth time, the fourth signal corresponding to a fourth sample value;

calculating a difference between the fourth sample value and the third sample value, the difference corresponding to a third delta value; and determining that the third delta value does not correspond to any of the k delta values.

14. The method of claim 13, further comprising:

encoding the sequence of the first delta value and the second delta value in response to the determination that the third delta value does not correspond to any of the k delta values.

15. The method of claim 13, further comprising:

determining that the node at the second depth and the second node index does not have any branches; and in response to determining that the node at the second depth and the second node index does not have any branches, encoding the sequence of the first delta value and the second delta value.

16. The method of claim 13, further comprising:

in response to determining that the third delta value does not correspond to any of the k delta values, comparing the minimum number of bits required to represent the third delta value to a first number of bits of a first fixed bit length token $\delta_B$ to determine whether the minimum number of bits is greater than the first number of bits.

17. The method of claim 16, further comprising:

in response to determining that the minimum number of bits is less than or equal to the first number of bits, encoding the third delta value as a $\delta_B$ token.

18. The method of claim 16, further comprising:

in response to determining that the minimum number of bits is greater than the first number of bits, comparing the minimum number of bits required to represent the third delta value to a second number of bits of a second fixed bit length token SC to determine whether the minimum number of bits is greater than the second number of bits.

19. The method of claim 18, further comprising:

in response to determining that the minimum number of bits is less than or equal to the second number of bits, encoding the third delta value as a SC token.

20. The method of claim 18, further comprising:

in response to determining that the minimum number of bits is greater than the second number of bits, encoding the fourth sample value as a sample token.

* * * * *

UNITED STATES PATENT AND TRADEMARK OFFICE
CERTIFICATE OF CORRECTION

| | | |
|---|---|---|
| PATENT NO. | : 11,923,876 B2 | |
| APPLICATION NO. | : 17/260396 | |
| DATED | : March 5, 2024 | |
| INVENTOR(S) | : Christopher L. Felton et al. | |

It is certified that error appears in the above-identified patent and that said Letters Patent is hereby corrected as shown below:

On the Title Page

Item (57) In The Abstract:
Lines 8-9, "the Leads root" should be --the root--.

In the Specification

Column 8, Lines 22-23, "of (values)" should be --of δ values)--.

Column 14, Eq. (5), Line 18, "$Emit_{NEW}$" should be --$Emit_{CUR}$--.

Column 16, Line 64, "SC" should be --$δ_C$--.

Column 17, Line 33, "δc" should be --$δ_C$--.

Column 18, Line 62, "(Na)" should be --($N_n$)--.

Column 18, Line 63, "δn" should be --$δ_n$--.

In the Claims

Claim 18, Column 24, Line 45, "SC" should be --$δ_C$--.

Claim 19, Column 24, Line 51, "SC" should be --$δ_C$--.

Signed and Sealed this
Second Day of July, 2024

Katherine Kelly Vidal
*Director of the United States Patent and Trademark Office*